(12) United States Patent
Gundermann et al.

(10) Patent No.: US 9,399,042 B2
(45) Date of Patent: Jul. 26, 2016

(54) METHOD FOR THE REMOVAL OF SUBCUTANEOUS FAT ACCUMULATIONS BY SUBCUTANEOUS LIPOLYSIS BY ADMINISTERING A COMBINATION OF GLYCYRRHIZIC ACID AND SOYBEAN PHOSPHOLIPIDS

(75) Inventors: Karl-Josef Gundermann, Köln (DE); Dirk Brandl, Albersloh (DE)

(73) Assignee: Lichtblick GmbH, Drensteinfurt (DE)

( * ) Notice: Subject to any disclaimer, the term of this patent is extended or adjusted under 35 U.S.C. 154(b) by 311 days.

(21) Appl. No.: 13/642,916

(22) PCT Filed: Apr. 28, 2011

(86) PCT No.: PCT/EP2011/056721
§ 371 (c)(1),
(2), (4) Date: Feb. 4, 2013

(87) PCT Pub. No.: WO2011/135020
PCT Pub. Date: Nov. 3, 2011

(65) Prior Publication Data
US 2013/0157967 A1 Jun. 20, 2013

(30) Foreign Application Priority Data
Apr. 29, 2010 (DE) .......................... 10 2010 028 365

(51) Int. Cl.
| | |
|---|---|
| *A61K 31/704* | (2006.01) |
| *A61K 31/66* | (2006.01) |
| *A61K 31/685* | (2006.01) |
| *A61K 31/683* | (2006.01) |

(52) U.S. Cl.
CPC .............. *A61K 31/704* (2013.01); *A61K 31/66* (2013.01); *A61K 31/685* (2013.01); *A61K 31/683* (2013.01)

(58) Field of Classification Search
None
See application file for complete search history.

(56) References Cited

U.S. PATENT DOCUMENTS

| 2005/0143347 A1* | 6/2005 | Boderke et al. .................. 514/78 |
| 2008/0286254 A1* | 11/2008 | Sakamoto et al. ......... 424/93.45 |
| 2010/0179100 A1 | 7/2010 | Guseva et al. |

FOREIGN PATENT DOCUMENTS

| CA | 2543187 | 5/2005 | |
|---|---|---|---|
| DE | 10349979 A1 | 6/2005 | |
| DE | 10361067 A1 | 7/2005 | |
| EP | 375082 B1 * | 3/1995 | ............... A61K 7/06 |
| JP | 2002-356434 | 12/2002 | |
| JP | 2007-509085 | 4/2007 | |
| JP | 2007-119441 | 5/2007 | |
| JP | 2009-242354 | 10/2009 | |
| WO | 2007/020505 | 2/2007 | |

OTHER PUBLICATIONS

Lim, W. Y., Chia, Y. Y., Liong, S. Y., Ton, S. H., Kadir, K. A., & Husain, S. N. (2009). Lipoprotein lipase expression, serum lipid and tissue lipid deposition in orally-administered glycyrrhizic acid-treated rats. Lipids Health Dis, 8(1), 31.*
Matarasso, A., & Pfeifer, T. M. (2009). Mesotherapy and injection lipolysis. Clinics in plastic surgery, 36(2), 181-192.*
Artegodan GmbH, "Lipostabil N i.v. 5 ml," Oct. 1, 2008, retrieved from internet, two pages.
International Search Report for corresponding PCT/EP2011/056721 mailed Jun. 22, 2011, three pages.
Espacenet bibliographic data for DE 10349979 published Jun. 16, 2005, one page.
Espacenet bibliographic data for DE 10361067 published Jul. 14, 2005, one page.
Luo et al., "Anti-obesity effect of glycyrrhizin on obese rats and its mechanism," Central South Pharmacy, 2010, vol. 8, No. 3, pp. 204-208 (in Chinese).
English translation of Luo et al., "Anti-obesity effect of glycyrrhizin on obese rats and its mechanism," Central South Pharmacy, 2010, vol. 8, No. 3, six pages.
Zhang et al., "Preliminary exploration in injecting phosphatidylcholine for fat-dissolving," Chinese Journal of Aesthetic Medicine, Dec. 2006, vol. 15, No. 12, pp. 1346-1348 (in Chinese).
English translation of Zhang et al., "Preliminary exploration in injecting phosphatidylcholine for fat-dissolving," Chinese Journal of Aesthetic Medicine, Dec. 2006, vol. 15, No. 12, three pages.
English Translation of JP 2007-119441, 40 pages.
English Translation of JP 2002-356434, 18 pages.
English Translation of JP 2009-242354, 23 pages.
Lim, et al. "Lipoprotein Lipase Expression, Serum Lipid and Tissue Lipid Deposition in Orally-Administered Glycyrrhizic Acid-Treated Rats", Lipids in Health and Disease, 2009, vol. 8, No. 31, pp. 1-10.

\* cited by examiner

*Primary Examiner* — Eric Olson
*Assistant Examiner* — Dale R Miller
(74) *Attorney, Agent, or Firm* — Rankin, Hill & Clark LLP

(57) ABSTRACT

The invention described herein relates to the use of an aqueous composition containing at least one phospholipid. at least one glycyrrhizic acid or salts of glycyrrhizic acid for the manufacture of mediciments for the removal of subcutaneous fat accumulation.

10 Claims, 12 Drawing Sheets

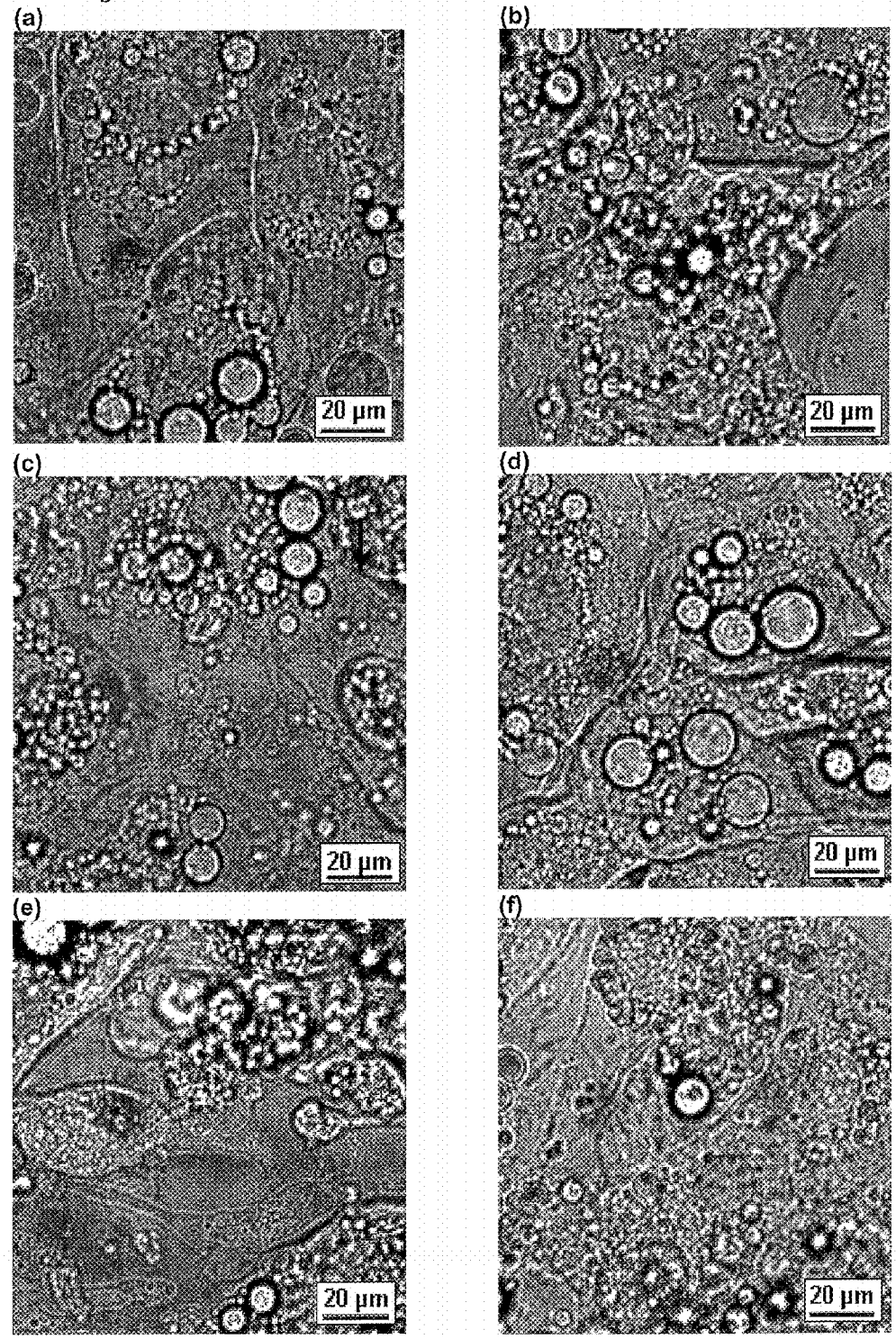

Fig. 8 (a-c)
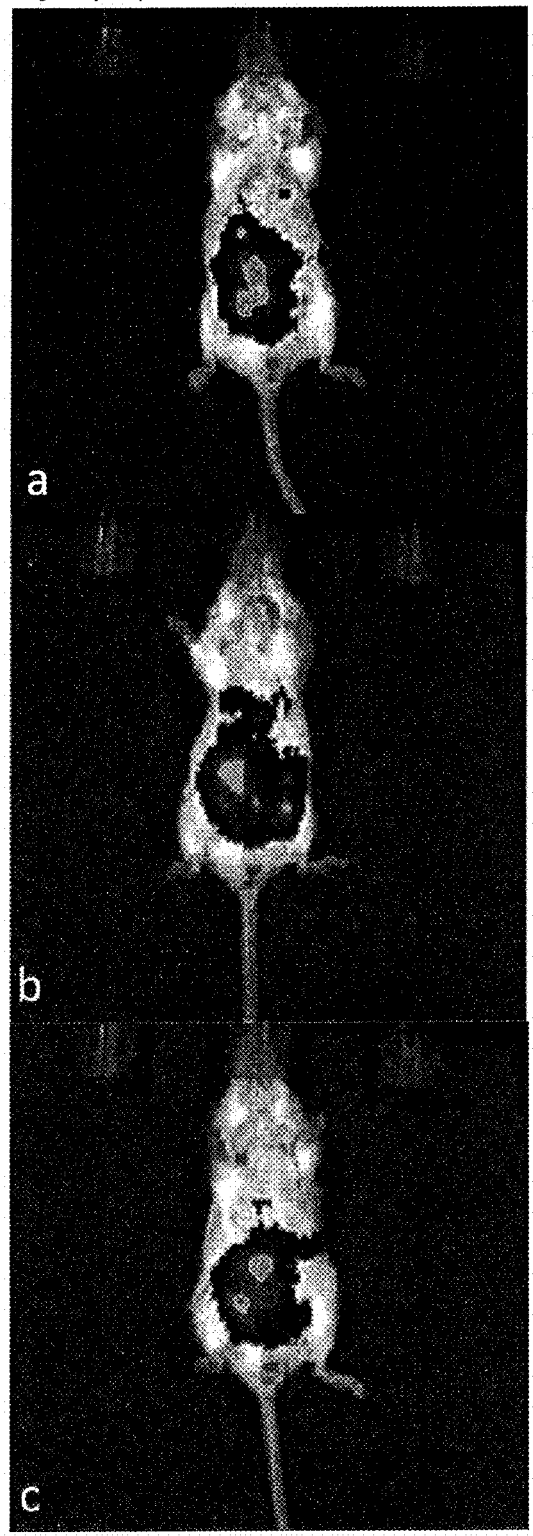
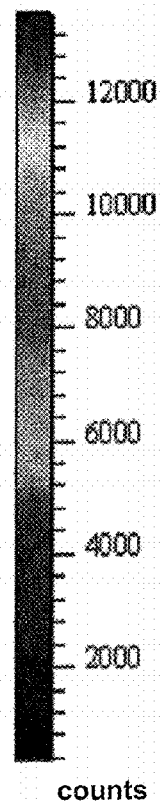

Fig. 8 (d-f)
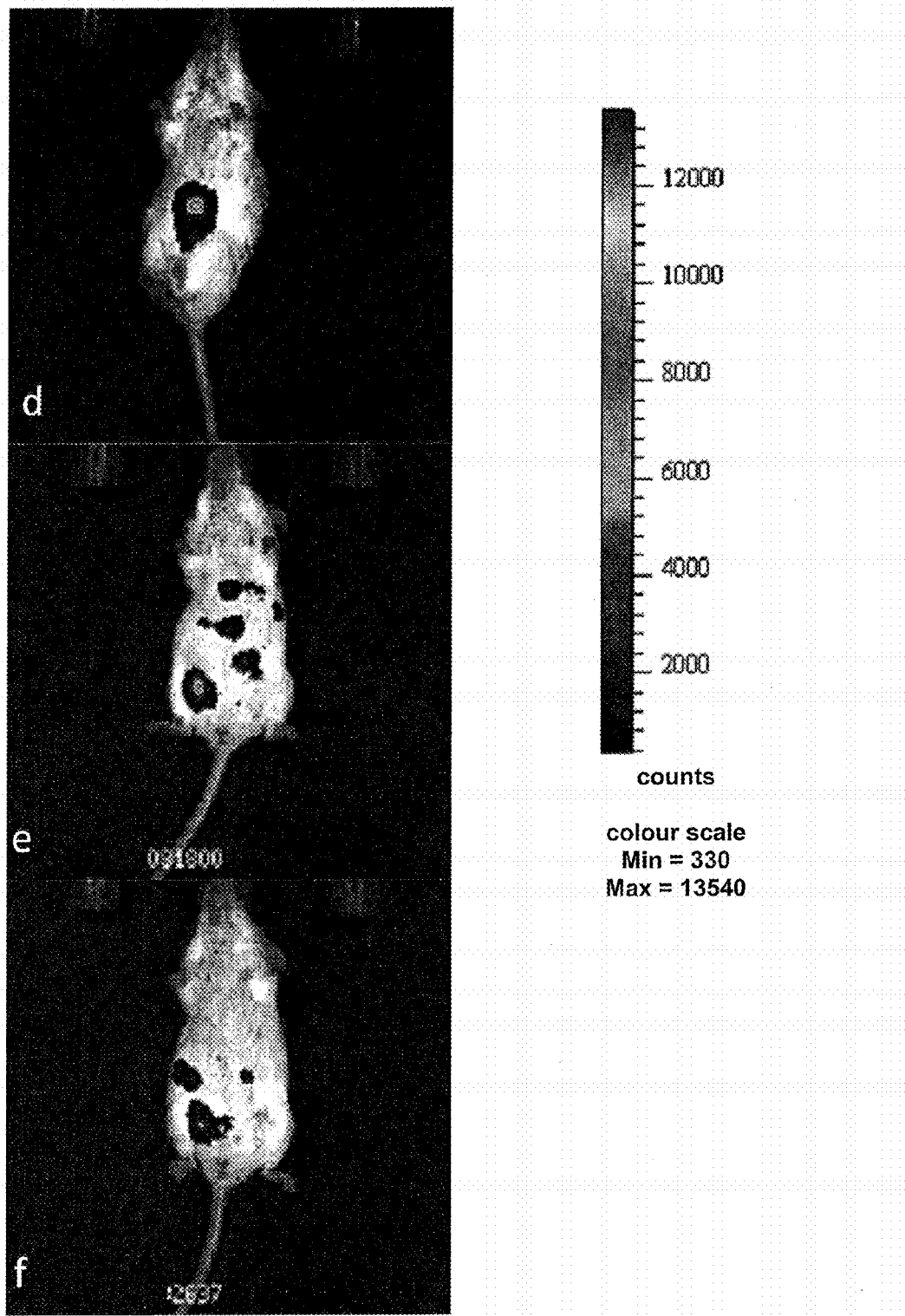

Fig. 8 (g-i)
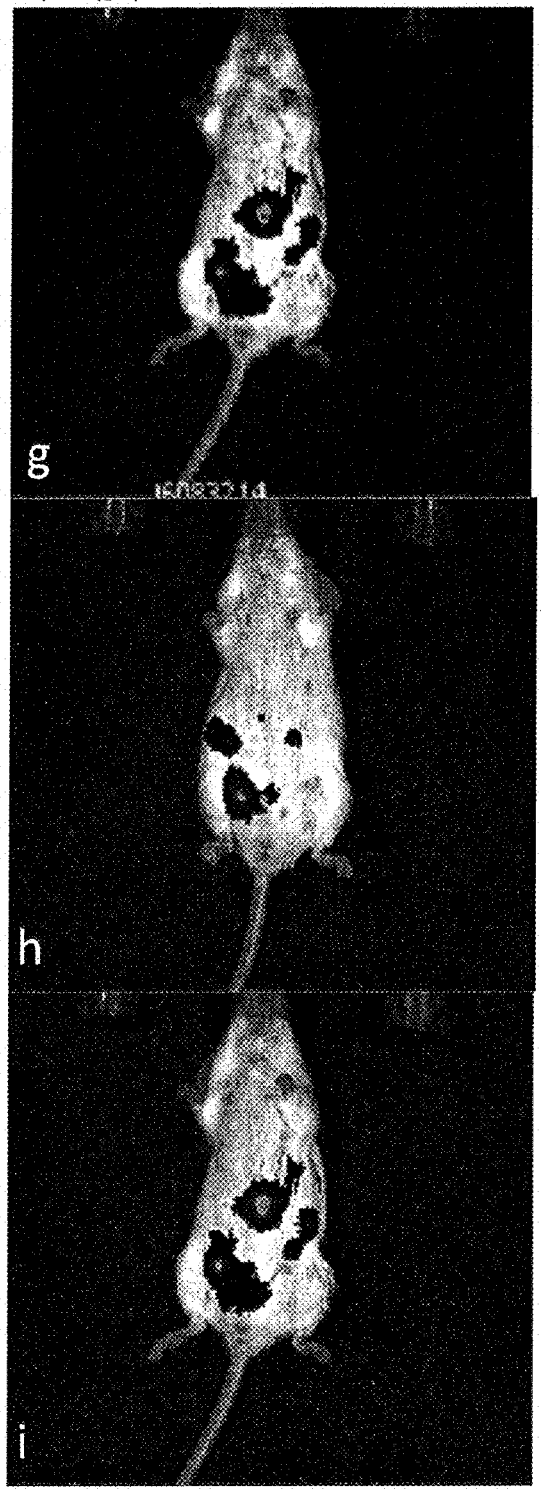
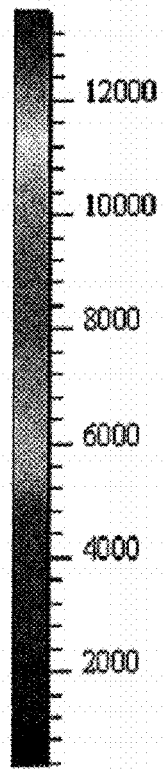
counts
colour scale
Min = 330
Max = 13540

Fig.10
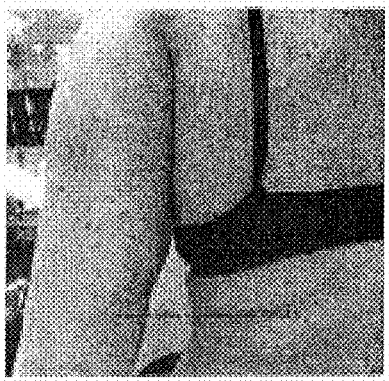
upper arm left (Phosphogliv®)
upper arm right (Lipostabil®)
Fig. 11
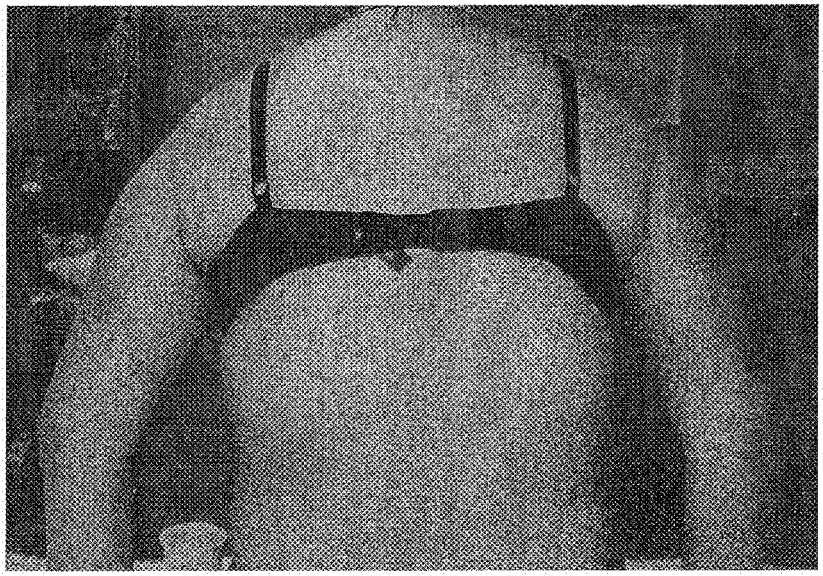
upper arm left (Phosphogliv®)　　　　upper arm right (Lipostabil®)

METHOD FOR THE REMOVAL OF SUBCUTANEOUS FAT ACCUMULATIONS BY SUBCUTANEOUS LIPOLYSIS BY ADMINISTERING A COMBINATION OF GLYCYRRHIZIC ACID AND SOYBEAN PHOSPHOLIPIDS

The invention relates to the use of a composition based on phospholipids and at least one glycyrrhizic acid or a salt of glycyrrhizic acid and its medicinally applicable forms, for the treatment of adipose deposits under the skin of various phenotypes such as subcutaneous distribution disturbances of fat, and for the regression of diet-resistant fat pads.

STATE OF THE ART

So far in the state of the art surgical methods were used to treat subcutaneous fat accumulation or abnormal growth of fat cells as lipomas or lipedemas. Such treatments lead to known complications or risks, caused by anesthesia, local reactions and possible infections. Often inpatient hospital stays are unavoidable in such circumstances. Non-surgical alternatives are sought for the removal of subcutaneous fat accumulations to avoid such operations.

Various phospholipid compounds have already been developed, which are administered by injection to patients. Aqueous formulations comprising at least one phospholipid are known for various applications. These systems are used for example in cosmetics or for the manufacture of pharmaceutical products. Frequently, these systems form micelles or liposomes containing an aqueous phase in their interior.

The US 2005/143347 A1 and the associated priority document DE 103 61 067 A1 disclose an aqueous composition containing at least one phospholipid and/or at least one bile acid and a component supporting fat decomposition as riboflavin and water, suitable for the manufacture of medicaments for the removal of subcutaneous fat accumulations and for the regression of fat pads. Therein Essentiale® N i.V. (Red List, March 2003) and Lipostabil® N i.V. are mentioned as commercially available preparations.

Essentiale® N i.V. is described in EP 0 615 746 A1 as an aqueous preparation containing phospholipids from soybean, bile acid, riboflavin, alpha-tocopherol, ethanol and water. The composition is processed in a micellar system, whereby the micelles have a diameter of 30 nm to 100 nm. In EP 0 615 746 A1 the use of a glycyrrhizic acid is not described. This preparation is administered intravenously to treat inter alia a fatty degeneration of the liver, which is an excessive fat content of the liver parenchyma (fatty deposits in the form of droplets).

In DE 103 61 067 A1 the aqueous formulation of the medicinal preparation Essentiale® N i.V. is disclosed containing at least one phospholipid and/or at least one bile acid and a component supporting fat decomposition and water for the manufacture of a medicament for the removal of subcutaneous fat accumulations. Here as well glycyrrhizic acid is not added to the preparation.

Lipostabil® N i.V. comprises phospholipids from soybean, DL-alpha-tocopherol, 7-deoxycholic acid, alcohols, other auxiliaries, and water. However, the active substance composition of this compound does not contain glycyrrhizic acid. By the subcutaneous injection of Lipostabil® N i.V. fat accumulations which appear at overweight people under the eyes, at the abdomen or hips are removed.

There are further preparations which are based on a phospholipid and are used for subcutaneous injection for the purpose of lipolysis of fat accumulations, which are described in WO 2008/113421, DE 10 2007 015 701, US 2005/143347 A1 and US 2005/0089555 A1.

Disadvantages of the above preparations of the prior art for a subcutaneous lipolysis include inter alia swelling, hematomas (bruises), pain in the treatment region and discomfort such as burning sensation and itching at the injection site after treatment, but in particular cell death by damaging the cell structure and membrane integrity (cell necrosis).

In efforts to find active compounds for the non-surgical removal of subcutaneous fat accumulations without the above mentioned disadvantages, it has now been surprisingly found, that the composition disclosed in RU 2133122 C1 for the intravenous and oral treatment of acute and chronic liver disease as well as disorders of the lipid metabolism in arteriosclerosis and associated diseases, is suitable for a subcutaneous lipolysis, also called adipocytolysis.

By the use according to the present invention of this composition which comprises at least one phospholipid, preferably a phosphatidyl choline, and one glycyrrhizic acid or its salt, the previously described disadvantages of the prior art preparations, which were used for subcutaneous lipolysis, are reduced and/or eliminated completely.

The particular advantage of the use of the claimed composition for the subcutaneous lipolysis of fat accumulation according to the present invention is the significant reduction to complete prevention of the damage of the cell structure and the membrane integrity of adipose tissue cells (adipocytes). In the inventive treatment of subcutaneous disorders of adipose tissue with the claimed composition the occurrence of necrosis is significantly reduced or prevented completely.

Through the inventive use depot fat in the body of the treated fat tissues is degraded by lipolysis without causing any destruction of the cell membrane.

Significantly fewer side effects are observed up to a complete absence of complaints such as swelling, redness, burning, itching and general pain and hypersensitivity.

The composition used according to the invention includes as the main components one phospholipid, glycyrrhizic acid or a salt thereof and if necessary at least one auxiliary.

Glycyrrhizic acid, which can be obtained from an extract from plants of the genus *Glycyrrhiza*, the licorice (e.g. *Glycyrrhiza glabra*), or their salts, in particular sodium or ammonium glycyrrhizinate, are described in the prior art as absorption enhancers for the transport of e.g. peptide hormones through the mucous membrane in EP 03 27 756 A. Also, the increase of the absorption of polypeptides by glycyrrhizic acid in transvaginal preparations is described in U.S. Pat. No. 5,238,917 A.

Additionally, the glycyrrhizic acid is known as an antibacterial and anti-inflammatory ingredient and as an emulsifier in the prior art from US 2004-076652 A, US 2009-169588 A, US 2007-053852 A, WO 08/046,791A, WO 08/046,795 A, WO 05/037239 A, EP 1676561A and JP 2006/137 670.

The specific function of glycyrrhizic acid in the transport of molecules across the cell membrane supports the particular advantage of the quick mode of action of the inventive use of the claimed composition. Due to the glycyrrhizic acid, the phospholipid can penetrate into the adipose tissue cells of the subcutis particularity well and quickly, whereby the aforementioned disadvantages such as necrosis are reduced or do not occur at all. The described swellings, hematomas, pains and discomfort after a treatment with a preparation of the prior art, particularly those including bile acids or salts thereof, are alleviated or do not occur at all in the combination with the glycyrrhizic acid. This improved tolerance is supported by the anti-inflammatory and antibacterial property of the glycyrrhizic acid.

Consequently, the present invention is characterized in that the claimed combination of at least one phospholipid, preferably a phosphatidyl choline, and one glycyrrhizic acid or its salt, shows much less to no cytotoxic effects and has improved tolerance in comparison with the compositions of the preparations Essentiale® and Lipostabil® from the prior art.

The invention relates to the use of a composition comprising
a) at least one phospholipid;
b) at least glycyrrhizic acid or
c) a salt of glycyrrhizic acid and
d) if necessary, auxiliaries
wherein
the total content of the phospholipids and the glycyrrhizic acid or its salts is 2-80 wt-%, and
the weight ratio between phospholipids and glycyrrhizic acid or its salts is from 30:1 to 0.5:1,
for the manufacture of a medicament for the removal of subcutaneous fat accumulations.

The invention further relates to the use of a preparation comprising the above composition, which contains phosphatidyl choline as a phospholipid.

The invention further relates to the use of a preparation comprising the above composition, which contains phosphatidyl choline of animal or plant origin.

The invention further relates to the use of a preparation comprising the above composition which contains potassium, sodium, ammonium, or magnesium salts or other suitable salts of glycyrrhizic acid.

The invention further relates to the use of a preparation comprising the above composition, which contains as a potential excipient a sugar, particularly maltose and/or its derivatives, sorbitol or lactose.

The invention further relates to the use of a preparation comprising the above composition, which contains phosphatidyl choline with a total amount of 15 to 98 wt-%, preferably 30 to 98 wt-%, more preferably 50 to 98 wt-%, particularly preferably 75 to 90 wt-%, and most preferably 75 to 98 wt-%.

The invention further relates to the use of a preparation comprising the above composition which is dissolved in dry form in a suitable solvent.

The invention further relates to the use of a preparation comprising the above composition, which is used in dry form, preferably as a lyophilisate obtained by freeze-drying.

The invention further relates to the use of a preparation comprising the above composition, which is used in the form of a solution.

The invention further relates to the use of a preparation comprising the above composition, which contains physiologically suitable solvents comprising water, physiological saline solution, glucose solution, monohydroxy alcohols such as ethanol, 2-propanol, n-propanol, polyhydroxy alcohols such as glycerol and/or propanediol, polyglycol such as polyethylene glycol and/or Miglyol, glycerol, formal, dimethyl isosorbitol, natural and synthetic oils and/or ethers.

The invention further relates to the use of a preparation comprising the above composition, which is used for the manufacture of a medicament for the treatment of subcutaneous fat accumulations, subcutaneous adipose tissue disorders, in particular associated with the local disturbance of fat distribution.

The invention further relates to the use of a preparation comprising the above composition, which is used for manufacture of a medicament for the decomposition and degeneration (regression) of adipose tissue tumors.

The administration of the inventive preparation takes place in the form of creams, ointments, gels, hydrogels, lotions, pastes, lyophilisates and solutions. The aqueous formulation in the form of various solutions is preferred.

The invention further relates to the use of a preparation comprising the above composition characterized in that the undesired fat distribution disturbances which are of aesthetic or pathological nature, are lipedemas, lipomas, lipomatosis of the abdomen, dermatopanniculosis deformans, pseudogynecomastia, Buffalo Hump of HIV patients, cellulitis, or non-specific subcutaneous fat depots.

The invention further relates to the use of a preparation comprising the above composition, characterized in that the administration of the preparation takes place by subcutaneous, intraperitoneal, intramuscular or intravenous injection.

The invention further relates to the use of a preparation comprising the above composition, characterized in that for the administration a method selected from the group consisting of iontophoresis, electroporation, microporation or phonophoresis is used.

Another object of the invention is the use of the composition for the manufacture of a medicament for the treatment of adipose tissue of the subcutis (lower dermis), in particular with local disturbance of fat distribution.

Another object of the invention is the use of the composition for the manufacture of a medicament for the regression and involution of adipose tissue tumors.

Another object of the invention is the use of the composition for the manufacture of a medicament for the treatment of undesired fat distribution disturbances in the subcutis of aesthetic or pathological nature, for example lipedemas, lipomas, lipomatosis of the abdomen, dermatopanniculosis deformans, pseudogynecomastia, Buffalo Hump in HIV Patients, cellulitis or nonspecific subcutaneous fat depots.

By the inventive use of the composition the above-mentioned risks and side effects of a surgical treatment or of a subcutaneous treatment with a preparation of the prior art, in particular those containing deoxycholic acid and its salts, can be avoided. Additionally, the outpatient treatment is more comfortable for the patients and less expensive compared to surgical treatment.

The above-described high therapeutic efficiency, which is evidenced by the rapid degradation of the fatty tissue through the composition, is connected to the synergistic effect of the interaction of the inventive combination of one phospholipid and/or one glycyrrhizic acid or a salt thereof. The inventive use of the presently claimed composition is characterized by significantly reduced side effects or in part by the absence of some of the previously described side effects.

Subcutaneous fat distribution disturbances are variations in the fatty tissue in the body of humans and mammals which occur as depot fat of genetic or dietary cause in the form of localized fat deposits and can be considered as aesthetically annoying critical areas, in particular abdomen, buttocks, hips, knees, calves, thighs, upper arms, chin, cheeks. Thereby, it can also deal with benign growths of fat cells such as lipomas (dystopic proliferation).

Adipose tissue disorders in the context of the present invention include for example the following disorders: lipoma (adipose tissue tumors), which are benign, slowly growing, usually spherical, possibly stalked (=L. pendulum) or even shaggy (=L. arborescens, such as the synovial) mesenchymal tumors from—enlarged—adipose tissue cells, preferably in the subcutaneous tissue, possibly centrally ossifying (=L. ossificans), blocked with phlegm (=L. myxomatodes) or calcified (=L. petrificans), also with increased formation of connective tissue and capsules (=L. fibrosum), blood vessel formation (=L. teleangiectodes), rarely malignant degenerating (=L. sarcomatodes, liposarcoma). These can be classified as pathological, because they grow and their connective tissue sheath in itself can be painful, as well as their generation of the compression of blood vessels causing nerve pains. This also includes the multiple lipomatosis, which leads to a heaped accumulation of lipomas in patients.

Morbus Dercum's disease, called lipomatosis dolorosa, is a special form of the hypertrophic proliferation of adipose tissue, which is located between the dermal fat fascia (Kampa's fat fascia) and the underside of the dermis. Hormonal effects lead to an enhanced water-binding capacity of those fat cells which in turn cause by pressure phenomena lymph tract obstructions in the area of initial fern-type lymph vessels, thereby exerting additional compression and irritation influences on the peripheral sensitive nerves, so that these patients have an extremely painful sensitivity to touch. In the course of several years to decades irregular fat nodules are formed, which are disseminated locally under the dermis, which is getting thinner due to aging and have a part painful and strong dysesthetic character.

The Madelung'sche fat neck (Lanois-Bensaude Syndrome) is a fatty tissue proliferating fatty tissue inflammation, which in addition to a dystrophic adipose tissue tumor formation also leads to scar-like connective tissue compression in the subcutaneous space. On this occasion surgical procedures are often only partially successful, because essential anatomical structures are involved in this process and the disorder is manifested essentially in the head, neck and shoulder area.

Lipedema is a painful swelling of the adipose tissue, which occurs especially on the lower legs of women and shows a progressive course and characteristics with increasing age.

The regression of lipolysis means the hydrolytic cleavage of fatty tissue and the involution by the mobilization of the proliferated fat area.

A xanthelasma is a yellowish accumulation of fat under the eyes.

HIV patients often have disturbances of fat tissue accumulations which occur due to the medication according to the state of the art, such as the Buffalo Hump-called bull neck in this patient group. Immune-compromised patients can generally not be exposed to a surgical removal, so the fat deposits remain and the patients stigmatize externally.

The above mentioned adipose tissue disorders show in contrast to the diet-related lipohypertrophy (which also results in a fat deposition in terms of fat distribution disturbance) pathologically clearly differentiating tissue changes or entities that are characterized by histological scarring and inflammation parameters, but also by connective tissue encapsulations and by changes in the histological adipose tissue morphology itself.

Another object of the invention is the use of the composition for the manufacturing of a medicament for the treatment of cellulite/-is. The cellulite is a special form of the hypertrophic proliferation of adipose tissue, which is located between the dermal fat fascia (Kampa's fat fascia) and the underside of the dermis. Hormonal effects lead to an enhanced water-binding capacity of those fat cells, which in turn due to pressure phenomena cause lymph tract obstructions in the area of initial fern lymph vessels. In the course of several years to decades irregular fat nodules are formed, which are disseminated locally under the dermis, which is getting thinner due to aging and have a part painful and strong dysesthetic character.

Another object of the invention is the use of the composition for manufacturing of a medicament for the treatment of pseudogynecomastia and lipomastia. Pseudogynecomastia is the fat accumulation in men around the mammary (breast) which leads to an enlargement of breast and is indicated first of all aesthetically. The lipomastia is a form of pseudogynecomastia without enlargement of the mammary gland corpus.

The phospholipids, which are contained in the pharmaceutical composition, which is herein described, can be produced from any animal or vegetable product, in particular from chicken eggs, oily seeds and fruits such as dried coconut, palm seeds, peanut, rapeseed, sunflower seeds, linseed, palm and/or olive oil. Best suited are the phospholipid obtained from soybean according to the procedures described in the European patents EP 0 054 770 B1 and EP 0 054 769 B1.

This phospholipid is highly purified and contains 15 to 98 wt-%, preferably 30 to 98 wt-%, more preferably 50 to 98 wt-%, particularly preferably 75 to 98 wt-%, most preferably 75 to 90 wt-% phosphatidyl choline. Such highly purified phospholipids may contain other components of phospholipids, in particular up to 15 wt-%, more preferably up to 12 wt-% phosphatidyl ethanolamine, up to 8 wt-% phosphatidic acid, up to 10 wt-% phosphatidyl inositol, up to 6 wt-% lysophosphatidyl choline or lysophosphatidyl ethanolamine, traces of phosphatidyl serine as well as other lipids in small quantities.

The invention also relates to the use of one glycyrrhizic acid or several glycyrrhizic acids, wherein the glycyrrhizic acid is present as a physiologically acceptable salt. As salts of the glycyrrhizic acid physiologically acceptable salts, in particular mono-, di- or trisodium salts or potassium salts, magnesium or ammonium salts are used. Mono-, di- or trisodium salts or potassium salts and ammonium salts are preferred and more preferred are mono-, di- or trisodium salts or potassium salts.

The mass ratio of the phospholipid to the glycyrrhizic acid is 30:1 to 0.5:1, preferably 15:1 to 0.5:1, more preferably 4:1 to 1:1, most preferably 3:1 to 2:1.

The phospholipid concentration in the composition is from 0.5 wt-% to 30 wt-%, preferably from 5 wt-% to 25 wt-%.

The recommended total content of the phospholipids and of the glycyrrhizic acid or its salt is deemed to be from 2-80 wt-%. In this a weight ratio between the phospholipids and the glycyrrhizic acid or its salt of 3:1 or 4:1 is preferred. At the weight ratios between the phospholipids and the glycyrrhizic acid or its salt of 2:1 to 3:1, the content of 2-45 wt-% of the phospholipids and the glycyrrhizic acid or its salt is preferred.

The pH value of the medicament is in the range from pH 6.0 to pH 9.0, preferably from pH 7.5 to pH 8.5, more preferably from pH 6.5 to pH 7.5 and in particular pH 6.5 to pH 7.0.

Where appropriate suitable auxiliaries are added. As pharmacologically acceptable auxiliaries sugars are provided, in particular maltose, glucose, lactose, sorbitol and mannitol and their derivatives, colloidal silicic acid and its derivatives, silica gel, talc, lactose, starch, gelatin, water, alcohols with one or more hydroxyl groups, in particular ethanol, glycerol and propyleneglycol, natural or synthetic oils, particularly petroleum, mineral oil, peanut oil, soybean oil, sesame oil, and ethers. Further suitable additives are cellulose, sucrose, malt, rice, fluorine, calcium, magnesium stearate, sodium stearate, glycerol monostearate, sodium chloride, and dried skim milk. Preferred auxiliaries especially for the subcutaneous lipolysis include water, alcohol, particularily ethanol, saline, maltose and aqueous dextrose.

The pharmaceutical composition described herein can be used in dry or liquid form.

Liquid forms include drops, solutions, suspensions, emulsions, injectable suspensions or injectable emulsions and liposome-micelle systems as well as liposome-micelle-water systems.

Liquid preparations as solutions, suspensions, emulsions, injectable suspensions or injectable emulsions are preferred. In particular injectable suspensions or injectable emulsions are preferred.

In particular liquid preparations such as solutions, suspensions, emulsions, injectable suspensions or injectable emulsions of the above mentioned ingredients, auxiliaries or solid substances which become immediately liquid after addition of water, another solvent or a suitable buffer, such as Tris buffer, can be used easily for injections. A lyophilisate is used preferably as the basis to obtain a liquid preparation.

By the use of the herein described pharmaceutical preparation as an injection it is recommended to use a suitable solvent which has no undesired side effects, e.g. water, saline, glucose, monohydroxy alcohols such as ethanol, 2-propanol, n-propanol, polyhydroxy alcohols such as glycerol and/or propanediole, polyglycol such as polyethylene glycol and/or Miglyol, glycerol, formal, dimethylisosorbitol, natural and synthetic oils and/or ethers, each alone or in combination, whereas for injections the use of liposomes-micelles systems is recommended.

The remaining volumes of alcohols after concentration should be from 0 percent by volume (vol. %) up to 20 vol. %, preferably from 0 vol. % to 10 vol. %.

The most appropriate application form of the herein described preparation is a mixture of active substances containing one phospholipid and the glycyrrhizic acid or its salt in the form of a liposome-micelle-water system. Such a liposome-micelle-water system that is designed for injections preferably has a pH value of 6.0 to 7.5.

The dry form of the herein described pharmaceutical preparation includes a lyophilisate, tablets, particularly film-coated tablets and pills, powders, capsules, granulate and dragees. A lyophilisate is preferred.

When the composition is produced in the form of a lyophilisate, the addition of water or Tris buffer leads to the formation of a water-liposome system that can be used for injecting.

The water-liposome system can also be filtered sterile and contains liposomes and micelles at a high concentration with a relatively small size of the particles of 30 nm to 180 nm, preferably 30 to 130 nm, particularly preferably 30 to 90 nm. These liposomes can be filtered sterile by using a filter with a pore diameter of 0.2 μm.

The preparation described herein, which is produced in the form of an aqueous solution, is preferably in the form of a liposome-micelle system, which is highly transparent, has a very long shelf life and can be filtered sterile. The system can be dried, for example by lyophilization, thereby resulting in a stable lyophilized mixture.

If the herein described pharmaceutical preparation is used as an injection solution, the application of a combination of active substances, which contains phospholipids and the trisodium salt of glycyrrhizic acid in a weight ratio between the phosphatidyl choline and the trisodium salt of the glycyrrhizic acid of 1:1 to 4:1 and preferably 2:1 to 3:1, is particularly recommended.

The manufacture of the inventive preparations is performed for example by dissolving or dispersing at least one phospholipid and at least one glycyrrhizic acid in the above mentioned ratio to each other in a suitable solvent. Afterwards the solution or dispersion is concentrated, and then water is added.

Methods for the manufacture of the preparations are also described in European Patent Applications EP 0 470 437 A or EP 0 615 746 A.

Where appropriate antioxidants such as ascorbic acid, sodium hydrogen sulfite or sodium pyrosulfite, alpha-tocopherol, preservatives such as benzyl alcohol or p-hydroxybenzoates or suspending agents as sodium carboxy methyl cellulose may be added to the preparations used according to the invention.

The preparations can optionally also contain colloidal structures such as micelles or mixed micelles. These structures have a particle diameter of 10 to 500 Å. They consist of glycyrrhizic acid and phospholipid. The mass ratio of glycyrrhizic acid to phospholipid is in wt-% from 0.1:2 to 2:1, preferably from 1:2. The phospholipid concentration in the colloidal structures in the medicament is from 5 wt-% to 15 wt-%, preferably 10 wt-%. The manufacture of the colloidal structures is performed for example by dissolving glycyrrhizic acid in water, whereby the solution becomes slightly alkaline. Then the phospholipid is dispersed therein. Finally it will be filtered.

The administration of the preparation used according to the invention and comparable dosage forms is performed by subcutaneous, intraperitoneal, intramuscular or intravenous injection. The subcutaneous injection is preferred.

Furthermore, the percutaneous administration is claimed, in various carrier media and by using various tools, such as iontophoresis.

The uniform insertion of the preparations and dosage forms used according to the invention may also occur in certain applications by a tumescence method which makes use of the hydrostatic pressure in order to ensure an uniform distribution.

Furthermore, percutaneous administration becomes possible, which can be performed in various carrier media such as creams, ointments, gels, hydrogels, lotions or pastes, and by using different tools, in particular iontophoresis, microporation, electroporation or phonophoresis.

Suitable preparations and dosage forms are e.g. suspensions, emulsions or injectable solutions as well as preparations with protracted release of active substance, in which manufacture common tools are used. The preparations may also be present as a concentrate, dry substance or lyophilisate, for example, to increase stability.

Preferbly, the pharmaceutical preparations are produced and administered in dosage units, whereby each unit contains as active constituent a certain dose of the preparation. For injection solutions in ampoule form, this dose may be per ml from about 10 mg up to about 2000 mg, preferably from about 50 mg up to about 2000 mg, more preferably from about 250 mg to 500 mg based on the phospholipid.

For the treatment of adult patients, depending on the size of the fat tissue to be treated, for the administration of injectable solutions daily doses of 5 mg to 2500 mg, preferably 250 mg to 2500 mg per injection session with max. 200 injections based on the phospholipid are necessary. The injectable solutions can also further be diluted before administration, preferably with a saline solution Under certain circumstances, however, higher or lower daily doses may be appropriate. The dose also depends on the size of the fat accumulations, for small lipomas quantities from 125 mg to 500 mg, preferably 250 mg to 500 mg per lipoma based on the phospholipid are completely sufficient. The administration of the daily dose can take place either in form of a single administration or as several smaller dose units, as also by multiple administration of subdivided doses at specific intervals.

The invention is explained in more detail through examples.

EXAMPLES

Example 1

Preparation of an Injection Solution for Subcutaneous Use

A solution of:
0.2 g (8%) trisodium salt of glycyrrhizic acid,
1.8 g (72%) maltose and
4.5 ml of water
were mixed thoroughly with a dispersion of
0.5 g (20%) phospholipid from soya and
0.5 ml (20%) 96-percent ethanol
under inert gas.

The total content of the phospholipid and the salt of glycyrrhizic acid was 28%. The ratio between the phospholipid and the salt of glycyrrhizic acid was 2.5:1.

The emulsion was dispersed by sonication (MSE Souiprep 150 disintegrator, England) at 4° C. for 30 seconds with a one minute break. After about 10 minutes a liposome suspension was formed.

The liposome suspension was filtered through a 0.2 µm filter and afterwards lyophilized.

The liposome suspension (5.0 ml) was freeze-dried within 5 hours (lyophilized). Thereby, about 2.5 g of a loose, slightly yellowish powder was obtained.

For a subcutaneous injection solution, 2.5 g of the preparation in ampoules were dissolved in 9.0 ml solvent (water or Tris buffer).

Example 2

Manufacture of a Liposome-Water System for Subcutaneous Use

A solution of 50 g of purified phospholipid from soya (82.5 wt.-% phospholipid+3.5 wt.-% phosphatidyl choline, up to 10 wt.-% phosphatidyl ethanolamine, 0.6 wt-% lysophosphatidyl choline and a maximum of 10 wt.-% of other lipids) and 0.25 g sodium salt of phosphatidyl glycerol was prepared in 250 ml ethanol. The prepared solution was reduced under vacuum.

The resulting mixture of phospholipids (approx. 20%) was dispersed in an inert gas stream by mixing with 500 ml of water, which already contained 20.0 g (7.99%) trisodium salt of glycyrrhizic acid and 180.0 g (71.92%) isomaltose.

The total content of the phospholipid and the salt of glycyrrhizic acid was 28.07%. The ratio between the phospholipid and the salt of glycyrrhizic acid was 2.5:1.

This dispersion was subjected five times to high pressure homogenization at 600 bar. The resulting liposome system was filtered with a filter of 0.2 µm and filled into ampoules of 10.0 ml under inert gas atmosphere. The product had the following characteristics:
Appearance: transparent, slightly opalescent liquid,
pH-value: 6.5,
Transparency (660 nm): 85%,
Average size of the particles (laser scattering): 75 nm,
Sterility: in accordance with the requirements,
Microscopic properties (cryofixation): 30-90 nm mostly monolamellar liposomes, single bilamellar liposomes.

The transparency of the preparation filled in ampoules was tested after 2, 6, 9 and 12 months of storage. There were no differences to the original clarity of the preparation 1.

Example 3

Investigation of a Membrane Damaging Effect of Phosphatidyl Choline on 3T3-L1 Cells In order to test in vitro the effects of phosphatidyl choline on the membrane integrity and stability, differentiated 3T3-L1 cells were incubated with different concentrations of phosphatidyl choline for 4 and 24 hours and then analyzed by light microscopy.

As a model system, the murine preadipocyte cell line 3T3-L1 was used for the studies. 3T3-L1 cells were stimulated to adipogenesis by a conventional hormone cocktail (corticosterone, isobutylmethylxanthine, indomethacin, insulin) and differentiated for another 8 days to mature adipocytes.

The mature adipocytes of the 3T3-L1 cells were treated with various concentrations of phosphatidyl choline.

First, a phosphatidyl choline stock solution was prepared: 500 mg/ml phosphatidyl choline dissolved in 70% ethanol The used concentrations of phosphatidyl choline were:
1 mg/ml, 5 mg/ml, 10 mg/ml, 15 mg/ml, 20 mg/ml

BRIEF DESCRIPTION OF THE DRAWINGS

FIG. 5 shows phase contrast images using a CLSM of treated differentiated 3T3-L1 cells in 2D cell culture.

FIG. 8 is bioluminescence images of luciferase-labelled cells after subcutaneous injection of ADSC into the right fat tissue of Balb/c mice.

FIG. 10 is photographic documentation after treatment of the left (Phosphogliv®) and right (Lipostabil®) upper arm of the test person.

FIG. 11 is photographic documentation after treatment of the left (Phosphogliv®) and right (Lipostabil®) upper arm of a second test person.

In FIG. 1a light microscopy images of 3T3-L1 cells after 24 hours of treatment with 1 mg/ml, 5 mg/ml, 10 mg/ml, 15 mg/ml and 20 mg/ml phosphatidyl choline are shown, and in FIG. 1b the detailed confocal laser scanning microscope (CLSM) images at a 63-fold magnification of 3T3-L1 cells treated with phosphatidyl choline can be seen. FIG. 1c shows propidium iodide (PI) stained 3T3-L1 cells after treatment with phosphatidyl choline.

FIG. 1a: Phase contrast images of treated differentiated 3T3-L1 cells in 2D cell culture. The treatment was as follows:
(a) control=untreated cells in differentiation medium
(b) 1 mg/ml of phosphatidyl choline after 24 hours
(b) 5 mg/ml of phosphatidyl choline after 24 hours
(d) 10 mg/ml of phosphatidyl choline after 24 hours
(e) 15 mg/ml of phosphatidyl choline after 24 hours
(f) 20 mg/ml of phosphatidyl choline after 24 hours
(Size bar=100 μm).

FIG. 1b: Phase contrast images using a CLSM at a 63-fold magnification of treated differentiated 3T3-L1 cells in 2D cell culture. The treatment was as follows:
(a) control=untreated cells in differentiation medium after 4 hours
(b) 1 mg/ml of phosphatidyl choline after 4 hours
(c) 5 mg/ml of phosphatidyl choline after 4 hours
(d) 10 mg/ml of phosphatidyl choline after 4 hours
(Size bar=20 μm).

FIG. 1c: Phase contrast (PC)-images using a CLSM at a 63-fold magnification of treated differentiated 3T3-L1 cells in 2D cell culture after PI staining. The treatment was as follows:
(a) control=untreated cells in ethanol
(b) positive control=untreated cells in differentiation medium+1% Triton
(c) 5 mg/ml of phosphatidyl choline after 4 hours
(d) 10 mg/ml of phosphatidyl choline after 4 hours
(e) 15 mg/ml of phosphatidyl choline after 4 hours After the incubation period (4 hours) the adipocytes were stained with 5 μg/ml PI and analyzed with CLSM. In the upper PI-row (a-e) the fluorescence images of PI-stained cells are shown. In the lower PC-row (a-e) the corresponding phase contrast images are presented with the overlapping fluorescence images over one another (size bar=20 μm).

Figure 1A:
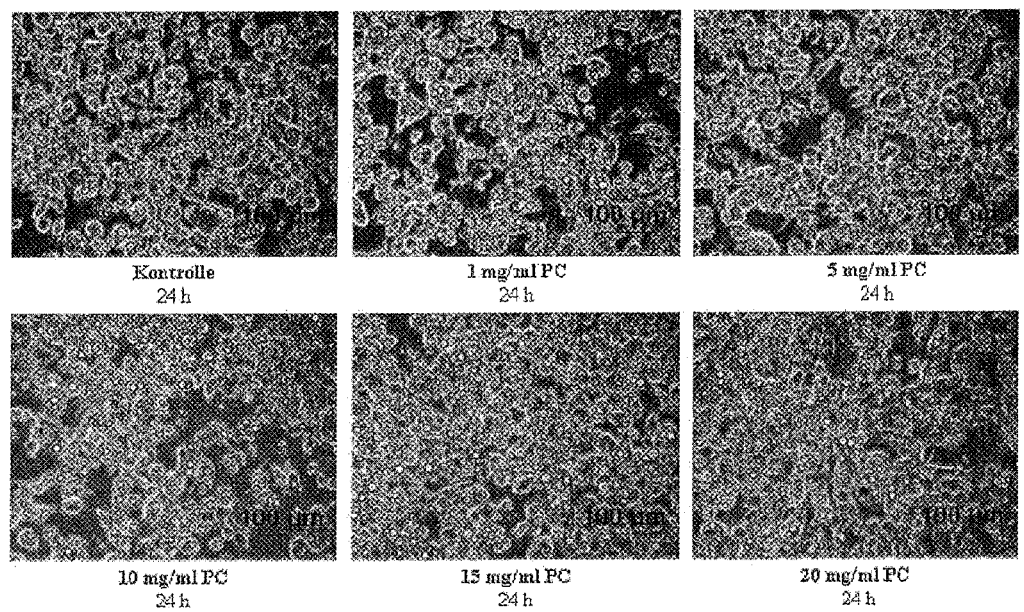
FIG. 1a shows light microscopy images of 3T3-L1 cells after 24 hours of treatment with 1 mg/ml, 5 mg/ml, 10 mg/ml, 15 mg/ml and 20 mg/ml phosphatidyl choline.
Figure 1B:
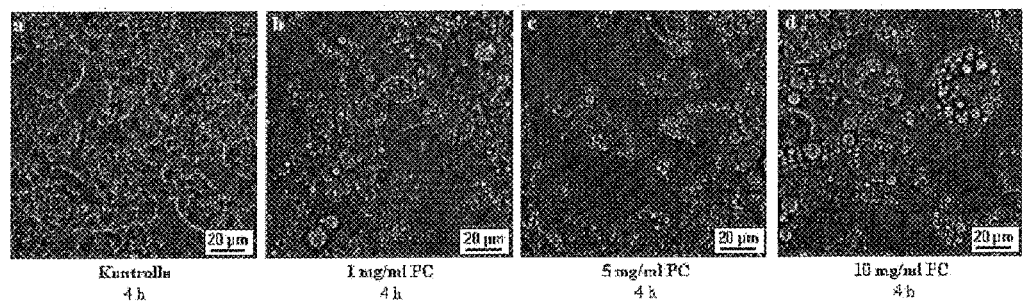
FIG. 1b shows phase contrast images using a CLSM at a 63-fold magnification of treated differentiated 3T3-L1 cells in 2D cell culture.

The cells treated with phosphatidyl choline (FIGS. 1a and 1b) show no morphological differences to untreated controls. Consequently, phosphatidyl choline has no cytotoxic effect. Comparable concentrations (20 mg/ml) of Na-deoxycholate caused a clear destruction of the cell membrane, which has not occurred at the used concentrations of phosphatidyl choline.

That phosphatidyl choline has no cytotoxic effect was confirmed by PI staining of the treated cells.

To this purpose differentiated 3T3-L1 were treated with 5 mg/ml, 10 mg/ml and 15 mg/ml phosphatidyl choline for 4 hours. Subsequently 5 g/ml PI were added for 5 minutes to the media and the cells were analyzed with the CLSM (FIG. 1c).

Figure 1C:
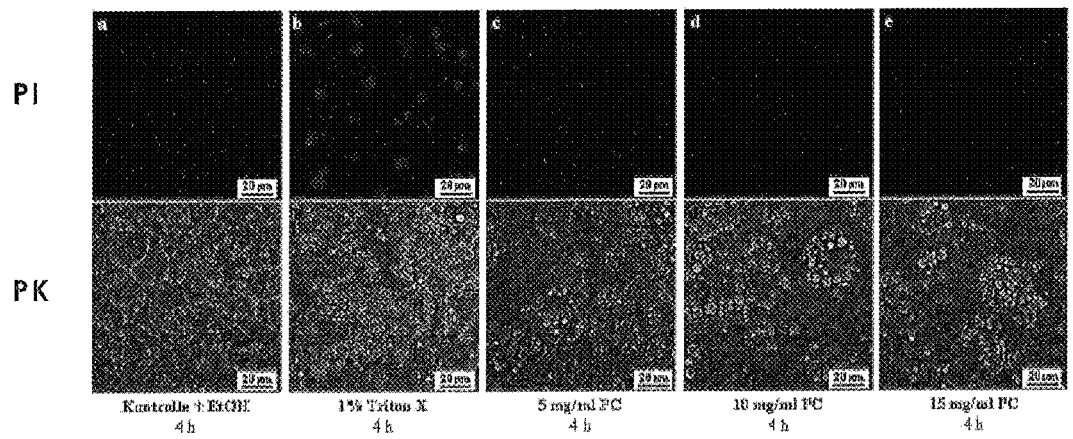
FIG. 1c shows phase contrast (PC)-images using a CLSM at a 63-fold magnification of treated differentiated 3T3-L1 cells in 2D cell culture after PI staining.

To the control (FIG. 1c, (a)) ethanol was added, so that the same concentration as in the solutions for the treatment of the cells was achieved. FIG. 1c (a) shows that no cells are stained with PI. It is concluded, that ethanol had no cytotoxic effect at the used concentrations.

In FIG. 1c (b) the positive control with 1% Triton shows numerous cells stained red by PI. This indicates an injury of the cell membrane. Here the membrane stability and integrity of the cell is damaged.

By comparison there are no red-stained cells detectable among the treated cells (FIG. 1c (c) to (e)). Consequently, these cells have no damage of the membrane stability and integrity. Accordingly, phosphatidyl choline has no damaging effect on differentiated 3T3-L1 cells.

This result correlates well with the light microscopic analysis (compare FIGS. 1a and 1b), wherein also no cell-damaging effect of phosphatidyl choline was observed Example 4

Extraction of "Adipose-Derived Stem Cells" (ADSC) from Human Subcutaneous Adipose Tissue In order to approach the clinical application, in further experiments a different model system with human mesenchymal stem cells was used.

Figure 2:
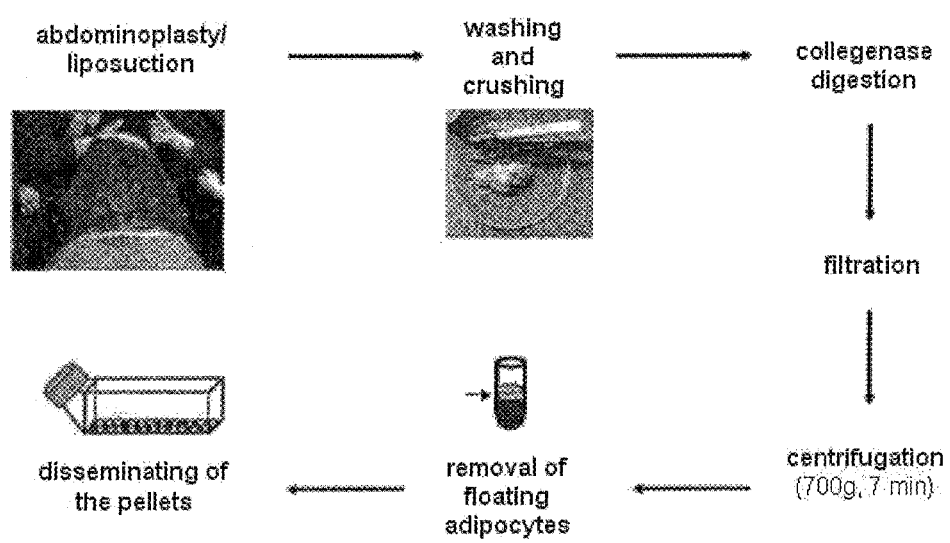
FIG. 2 schematically shows the isolation of ADSCs from human subcutaneous adipose tissue which is removed during plastic reductive surgery.

The human subcutaneous adipose tissue can serve as a potential source of adult stem cells. These so-called "Adipose-Derived Stem Cells" (ADSC) are multipotent and may be differentiated by appropriate stimuli into various cell types, e.g. osteoblasts, chondrocytes, adipocytes. The isolation of ADSCs from human subcutaneous adipose tissue which is removed during plastic reductive surgery, is shown schematically in FIG. 2.

First the fat was washed with buffer to remove hematopoietic cells, and then crushed. The resulting pieces of fatty tissue were digested with collagenase. By centrifugation of the digested tissue the stromal-vascular fraction was separated and the floated mature adipocytes were discarded. The stromal-vascular fraction in the pellet is composed of a heterogeneous cell population of blood cells, fibroblasts, pericytes, endothelial cells and preadipocytes.

This cell population was transferred into a culture bottle with medium, wherein a portion of the cells adhered. By adding a suitable cocktail consisting of insulin, dexamethasone, indomethacin and isobutylmethylxanthine or consisting of insulin, cortisol, troglitazone, triiodothyronine and isobutylmethylxanthine the cells were stimulated for adipogenesis and an improved adipogenic differentiation was achieved.

Example 5

Investigation of a Membrane Damaging Effect of Phosphatidyl Choline and Sodium Deoxycholate of ADSCs Na-deoxycholate (Na-DC)

The ADSCs of Example 4 were stimulated by a hormone cocktail (insulin, cortisol, troglitazone, triiodothyronine and isobutylmethylxanthine) to adipogenesis and then differentiated for another 21 days into mature adipocytes.

This was followed by a treatment with sodium deoxycholate. For this the following concentrations were used:
0.01 mg/ml, 0.05 mg/ml, 0.075 mg/ml, 0.1 mg/ml and 0.5 mg/ml.

As a control, untreated ADSCs were used.

The incubation period was 4 hours.

Figure 3A:
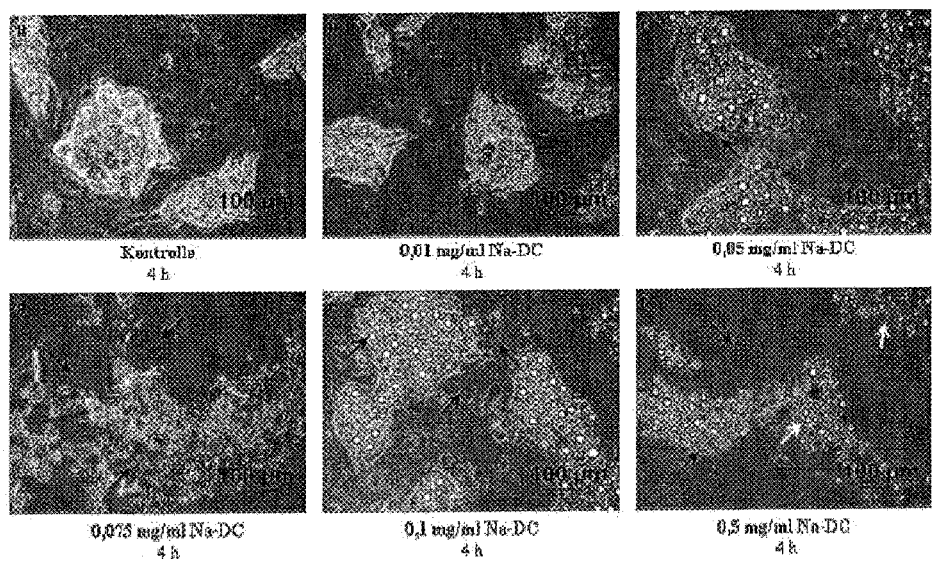
FIG. 3a shows light microscopy view of 3T3-L1 after an incubation period of 4 hours.

This concentration range has been already proven to be effective in 3T3-L1. After the incubation period of 4 hours, the differentiated treated cells were subsequently viewed by light microscopy (FIG. 3a).

Additionally, ADSCs treated with sodium deoxycholate were examined with CLSM. The differentiated, mature adipocytes were treated with:

0.01 mg/ml, 0.05 mg/ml and 0.1 mg/ml sodium deoxycholate for 4 hours.

As a control untreated ADSCs were used.

Figure 3B:
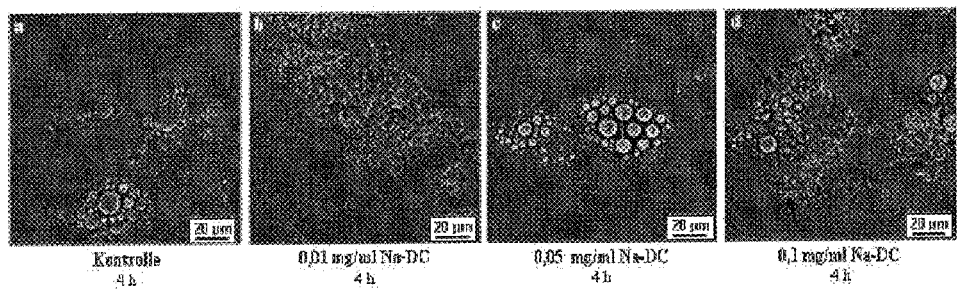
FIG. 3b shows microscopic analysis of ADSCs treated with deoxycholate with CLSM at a 63-fold magnification.

This was followed by microscopic analysis with CLSM at a 63-fold magnification (FIG. 3b).

Further analysis of the cell-damaging effect of sodium deoxycholate on ADSCs was performed by PI staining of the treated cells and subsequent analysis with CLSM. The differentiated, mature adipocytes were treated with:
0.05 mg/ml, 0.1 mg/ml and 0.5 mg/ml sodium deoxycholate for 4 hours.

As a control untreated ADSCs were used.

Then the cells were incubated in a medium containing 5 g/ml propidium iodide for 5 minutes. This was followed by microscopic analysis with CLSM at a 63-fold magnification (FIG. 3c).

FIG. 3a: light microscopic images of differentiated ADSCs after treatment with various concentrations of sodium deoxycholate (Na-DC) in 2D cell culture. The treatment was as follows:
(a) control=untreated cells in differentiation medium 4 hours
(b) 0.01 mg/ml Na-DC after 4 hours
(c) 0.05 mg/ml Na-DC after 4 hours
(d) 0.075 mg/ml Na-DC after 4 hours
(e) 0.1 mg/ml Na-DC after 4 hours
(f) 0.5 mg/ml Na-DC after 4 hours
Black arrows point at cells with damaged membrane or at cell fragments. White arrows indicate free lipid droplets.
(Size bar=100 µm).

FIG. 3b: CLSM images of differentiated ADSCs after treatment with various concentrations of sodium deoxycholate (Na-DC) in 2D cell culture. The treatment was as follows:
(a) control=untreated cells in differentiation medium 4 hours
(b) 0.01 mg/ml Na-DC after 4 hours
(c) 0.05 mg/ml Na-DC after 4 hours
(d) 0.1 mg/ml Na-DC after 4 hours
Black arrows point at cells with damaged membrane or cell fragments. White arrows indicate free lipid droplets.
(Size bar=20 µm).

Figure 3C:
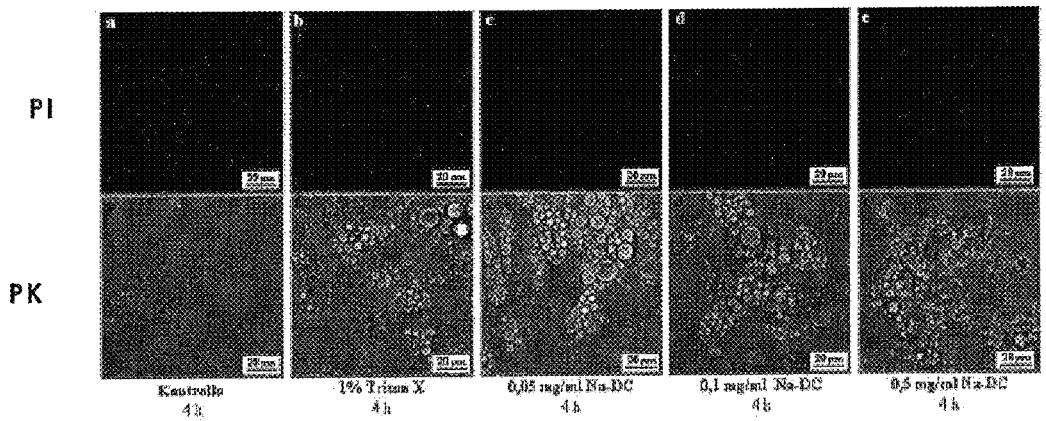
FIG. 3c shows microscopic analysis of ADSCs treated with propidium iodide with CLSM at a 63-fold magnification.

FIG. 3c: Confocal laser scanning microscopic images of differentiated ADSCs after treatment with various concentrations of sodium deoxycholate (Na-DC) in 2D cell culture. The treatment was as follows:
(a) control=untreated cells in differentiation medium 4 hours
(b) positive control=untreated cells in differentiation medium+1% Triton
(c) 0.05 mg/ml Na-DC after 4 hours
(d) 0.1 mg/ml Na-DC after 4 hours
(e) 0.5 mg/ml Na-DC after 4 hours After the incubation period (4 hours) the adipocytes were stained with 5 µm/ml PI and analyzed with CLSM. In the upper PI-row (a-e) fluorescence images of PI-stained cells are shown. In the lower PK-row (a-e) the corresponding phase contrast images are presented with the overlapping fluorescence images over one another.
(Size bar=20 µm).

A very low sodium deoxycholate concentration of 0.01 mg/ml had no effect on the cells (FIG. 3a (b)). No differences from the control group (FIG. 3a (a)) were seen. The adipocytes were vital and had an intact cell membrane. An increase of the concentration from 0.05 mg/ml already led to slight damages of the cell membrane (FIG. 3a (c)). This was reinforced at the next higher concentration (FIG. 3a (d, e)). The highest dose of 0.5 mg/ml exercised a significantly toxic effect on the cells (FIG. 3a (f)). The adipocytes were dead, the cell membrane was completely destroyed, so that basically only free lipid droplets and cell fragments were present. The effect of sodium deoxycholate on the ADSCs did not differ from that on the 3T3-L1. It could be set up identical dose-effect relationships. In both model systems at 0.05 mg/ml sodium deoxycholate membrane-damaging effects occurred, and a concentration of 0.5 mg/ml was found to be highly toxic.

By the more detailed inspection of the treated cells with the confocal microscope the previously made observations could be confirmed. While a low concentration of 0.01 mg/ml sodium deoxycholate (FIG. 3b (b)) showed no cytotoxic effect to the cell, a concentration of 0.1 mg/ml (FIG. 3b (d)) caused strong membrane damage. This proves a distinct membrane damaging effect of the Na-deoxycholate.

This effect was confirmed again by staining ADSCs cells after treatment with sodium deoxycholate with propidium iodide.

The positive control with 1% Triton clearly showed red cells stained by PI, indicating membrane damaged cells (FIG. 3c (b)).

After a treatment with 0.05 mg/ml sodium deoxycholate no red-stained cells and thus no cells with damaged membrane integrity and stability were detected (FIG. 3c (c)). After a treatment with 0.1 mg/ml sodium deoxycholate individual red-stained cells and thus few cells with damaged membrane integrity and stability were detectable (FIG. 3c (d)). After a treatment with 0.5 mg/ml sodium deoxycholate many and clearly red-stained cells and thus many cells with damaged membrane integrity and stability were detectable (FIG. 3c (e)).

This clearly shows a membrane damaging effect of the sodium deoxycholate concentration of 0.5 mg/ml to ADSCs.

Phosphatidyl Choline (PC)

Analogous to the experiments with Na-deoxycholate phosphatidyl choline was also investigated for a membrane damaging effect.

For this purpose similarly to the experiments with Na-deoxycholate the ADSCs from Example 4 were used and differentiated by a hormone cocktail (insulin, cortisol, troglitazone, triiodothyronine and isobutylmethylxanthine) to mature adipocytes.

Then the treatment was performed with phosphatidyl choline. For this the following concentrations were used:
1 mg/ml, 5 mg/ml, 10 mg/ml, 15 mg/ml and 20 mg/ml As a control untreated ADSCs were used.

The incubation period was 4 hours.

Figure 4A:
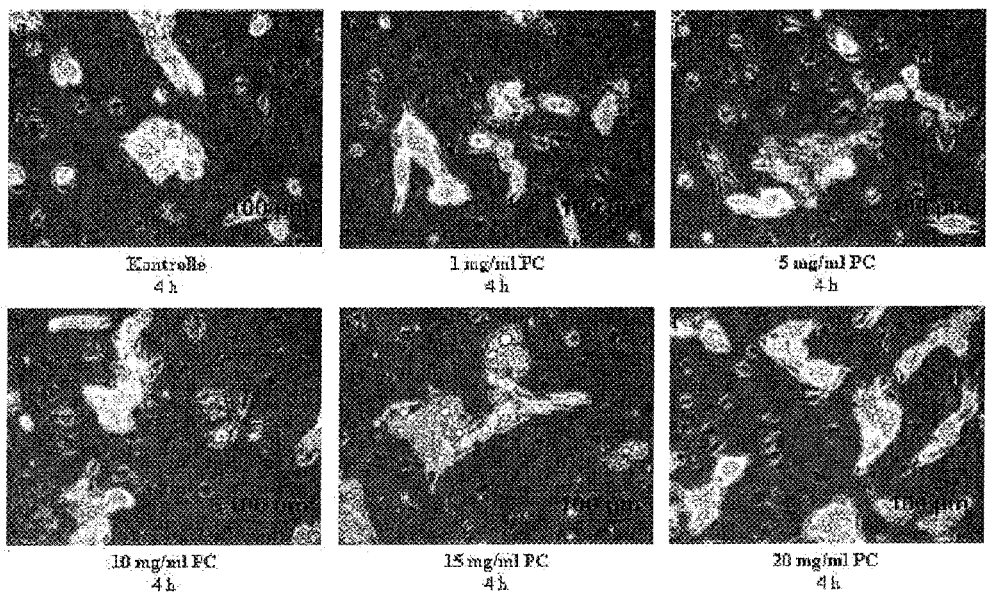
FIG. 4a shows differentiated treated cells after 4 hours of incubation as viewed by light microscopy.

This concentration range has already been proven to be effective in 3T3-L1. After the incubation period of 4 hours the differentiated treated cells subsequently were viewed by light microscopy (FIG. 4a).

Additionally with phosphatidyl choline treated ADSCs were examined with CLSM.

The differentiated, mature adipocytes were treated with:
1 mg/ml, 5 mg/ml and 15 mg/ml phosphatidyl choline for 4 hours.

As a control untreated ADSCs were used.

Figure 4B:
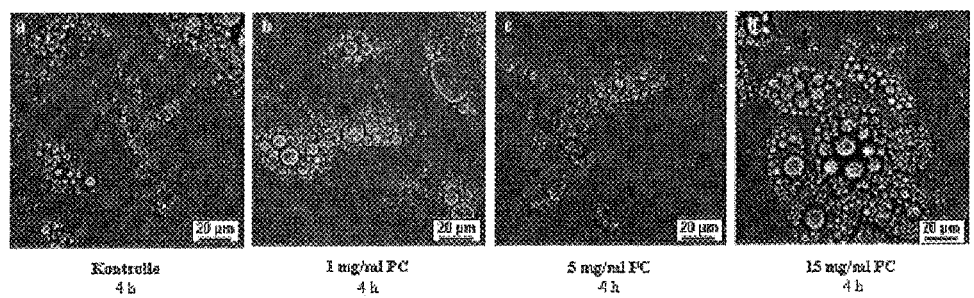
FIG. 4b shows the cells of FIG. 4A by microscopic analysis with CLSM at a 63-fold magnification.

This was followed by microscopic analysis with CLSM at a 63-fold magnification (FIG. 4b).

A further analysis of a cell-damaging effect of phosphatidyl choline on ADSCs was performed by PI staining of the treated cells and subsequent analysis with CLSM. The differentiated, mature adipocytes were treated with:
5 mg/ml, 10 mg/ml and 15 mg/ml phosphatidyl choline for 4 hours.

As a control untreated ADSCs were used.

Then the cells were incubated in a medium containing 5 µg/ml propidium iodide for 5 minutes. This was followed by microscopic analysis with CLSM at a 63-fold magnification (FIG. 4c).

FIG. 4a: light microscopic images of differentiated ADSCs after treatment with various concentrations of phosphatidyl choline (PC) in 2D cell culture. The treatment was as follows:
(a) control=untreated cells in differentiation medium 4 hours
(b) 1 mg/ml PC after 4 hours
(c) 5 mg/ml PC after 4 hours
(d) 10 mg/ml PC after 4 hours
(e) 15 mg/ml PC after 4 hours
(f) 20 mg/ml PC after 4 hours
(Size bar=100 μm).

FIG. 4b: CLSM images of differentiated ADSCs after treatment with various concentrations of phosphatidyl choline (PC) in 2D cell culture. The treatment was as follows:
(a) control=untreated cells in differentiation medium 4 hours
(b) 1 mg/ml PC after 4 hours
(c) 5 mg/ml PC after 4 hours
(d) 15 mg/ml PC after 4 hours
(Size bar=20 μm).

Figure 4C:
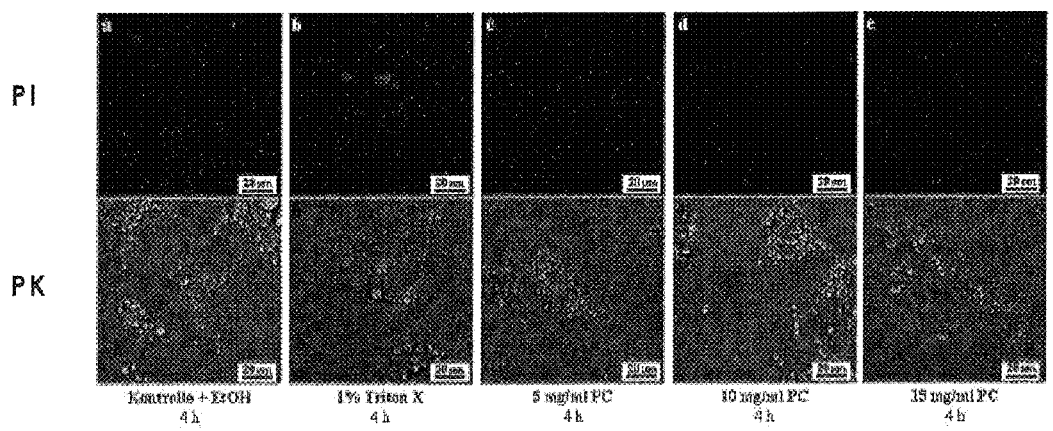
FIG. 4c shows the cells of FIG. 4a after incubation with propridium iodide with CLSM at a 63-fold magnification.

FIG. 4c: CLSM images of differentiated ADSCs after treatment with various concentrations of phosphatidyl choline (PC) in 2D cell culture. The treatment was as follows:
(a) control=untreated cells in differentiation medium 4 hours
(b) positive control=untreated cells in differentiation medium+1% Triton
(c) 5 mg/ml PC after 4 hours
(d) 10 mg/ml PC after 4 hours
(e) 15 mg/ml PC after 4 hours After the incubation period (4 hours) the adipocytes were stained with 5 μg/ml PI and analyzed with CLSM. In the upper PI-row (a-e) fluorescence images of PI-stained cells are shown. In the lower PK-row (a-e) the corresponding phase contrast images are presented with the overlapping fluorescence images over one another (Size bar=20 μm).

Corresponding to the observation in 3T3-L1 (Example 3) in the ADSC-cell model for phosphatidyl choline no cytotoxic effect (FIG. 4a) was established. Regardless of the PC concentration, the cells are vital and show no morphological changes.

In comparison, for Na-DC already at a concentration of 0.05 mg/ml Na-DC an injury was demonstrated and at a concentration of 0.5 mg/ml the ADSCs were dead (FIG. 3c).

An observation of ADSCs after treatment with phosphatidyl choline with CLSM confirmed, that no injury to the cells (4b) was present. Both the untreated control as well as the ADSCs treated with 15 mg/ml showed an intact morphology. Consequently phosphatidyl choline has no cytotoxic effect.

PI staining of ADSCs treated with phosphatidyl choline confirmed that phosphatidyl choline has no cytotoxic effects in vitro.

The positive control with 1% Triton clearly showed red cells stained by PI, indicating membrane damaged cells (FIG. 4c (b)).

After treatment with 5, 10 and 15 mg/ml sodium deoxycholate and after each PI staining no red-stained cells and thus no cells with damaged membrane integrity and stability were detectable (FIG. 4c (c) to (e)).

This clearly shows that treatment with phosphatidyl choline has no membrane damaging effect on ADSCs.

In contrast, the membrane integrity and stability of ADSCs was significantly damaged by Na-deoxycholate (FIG. 3c (d e)).

The experiments with Na-deoxycholate and phosphatidyl choline show that only Na-deoxycholate has a cytotoxic effect, but not phosphatidyl choline. Phosphatidyl choline does not cause damage to cell membranes or cells. These observations were confirmed by using several methods such as light microscopy, propidium iodide staining followed by fluorescence microscopy.

The effect of the substances did not change during the studied period over time; an incubation of 2 hours already showed the same effects as a 24-hour incubation. The experiments with Na-deoxycholate showed that this bile salt is membrane destabilizating and necrotic. After assessment of the required doses in vitro it is likely that the amounts of Na-deoxycholate used in vivo are cytotoxic.

For phosphatidyl choline in vitro no cytotoxic effect could be demonstrated, which also probably will be the case in vivo. This phospholipid was not cytotoxic.

Example 6

Investigation on the Combination of Phosphatidyl Choline, Glycyrrhizinate and Maltose The effect of a new substance combination was studied. This combination consists of
50 mg/ml phosphatidyl choline (PC)
20 mg/ml trisodium glycyrrhizinate, and
180 mg/ml maltose.

At first, dose-response relationships with respect to membrane damaging and cytotoxic effects were determined, and tests for lipolytic activity were conducted.

As a model system the murine preadipocyte cell line 3T3-L1 was used for the studies. 3T3-L1 cells were stimulated by a hormone cocktail (corticosterone, isobutylmethylxanthine, indomethacin, insulin) to adipogenesis and differentiated for another 8 days to mature adipocytes.

The mature adipocytes of 3T3-L1 cells were incubated with various concentrations of phosphatidyl choline between 0.1 mg/ml and 50 mg/ml. The phosphatidyl choline was combined with 2-20 mg/ml glycyrrhizinate and 18-180 mg/ml maltose.

The incubation of mature 3T3-L1 cells was performed for a duration of 4 hours with the substances combination.

Then the treated cells were examined at a 63-fold magnification by light microscopy for a membrane destabilizing and cytotoxic effect.

Figure 6:
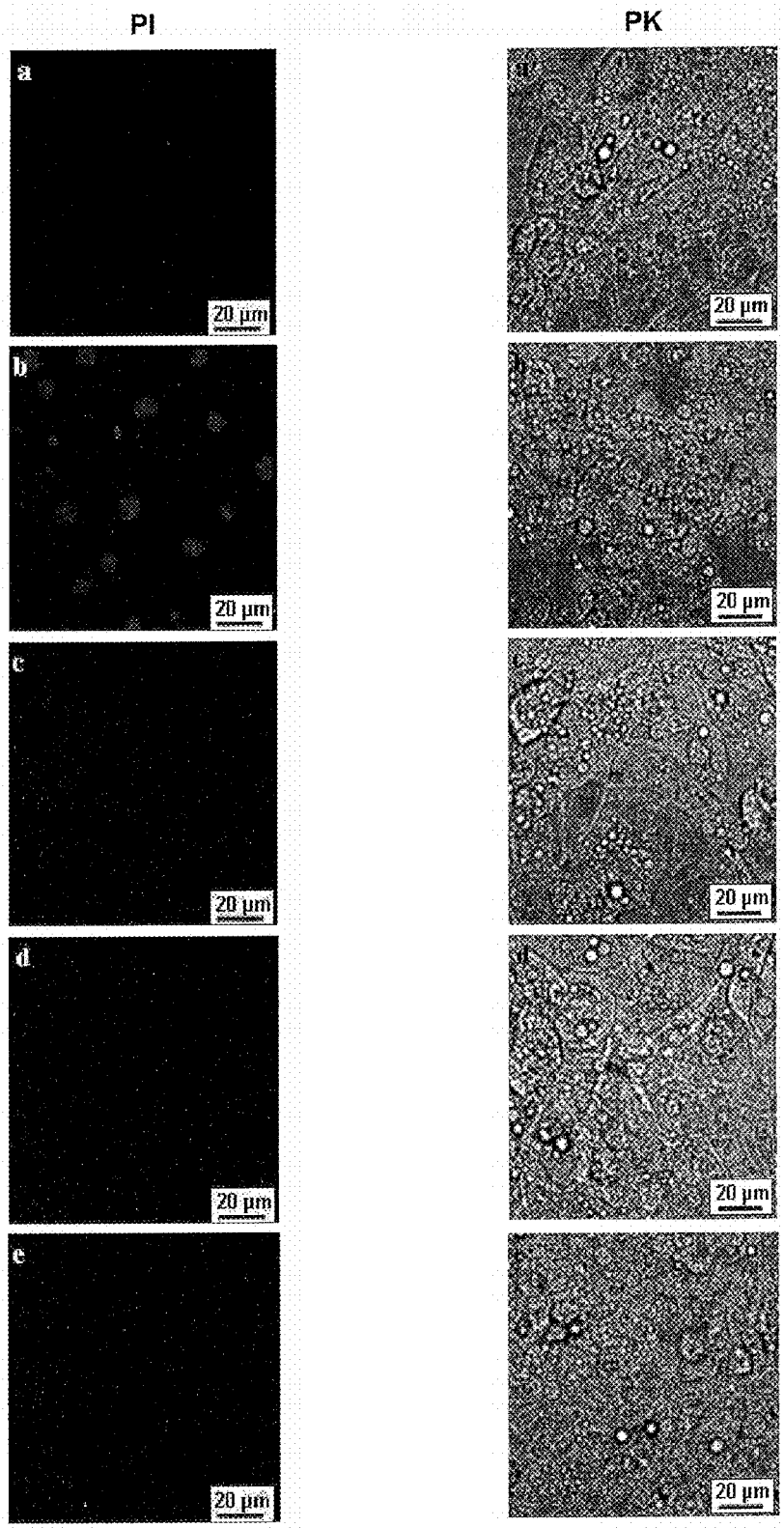
FIG. 6 shows images using a CLSM of treated differentiated 3T3-L1 cells in 2D cell culture.

The results are shown in FIGS. 5 and 6:

FIG. 5: Phase contrast images using a CLSM of treated differentiated 3T3-L1 cells in 2D cell culture. The treatment was as follows:
(a) control=untreated cells in differentiation medium
(b) 5 mg/ml PC+2 mg/ml glycyrrhizinate+18 mg/ml maltose
(c) 10 mg/ml PC+4 mg/ml glycyrrhizinate+36 mg/ml maltose
(d) 20 mg/ml PC+8 mg/ml glycyrrhizinate+72 mg/ml maltose
(e) 30 mg/ml PC+12 mg/ml glycyrrhizinate+108 mg/ml maltose
(f) 50 mg/ml PC+20 mg/ml glycyrrhizinate+180 mg/ml maltose
(Size bar=20 μm).

FIG. 6: Images using a CLSM of treated differentiated 3T3-L1 cells in 2D cell culture. The treatment was as follows:
(a) negative control=untreated cells in differentiation medium
(b) positive control=untreated cells in differentiation medium+1% Triton X
(c) 20 mg/ml PC+8 mg/ml glycyrrhizinate+72 mg/ml maltose
(d) 30 mg/ml PC+12 mg/ml glycyrrhizinate+108 mg/ml maltose
(e) 50 mg/ml PC+20 mg/ml glycyrrhizinate+180 mg/ml maltose After the incubation period (4 hours) the adipocytes were stained with 5 μg/ml PI and analyzed with CLSM. in the left PI-column (a-e) fluorescence images of PI-stained cells are shown. In the right PK-column (a-e) the corresponding phase contrast images are presented with the overlapping fluorescence images over one another (Size bar=20 µm).

The adipocytes treated with the substance combination did not differ from control cells (control FIG. 5a). Under the light microscope they showed the same morphology as the cells of the control, they were vital and had an intact cell membrane. The substance combination had no visible membrane damaging effects on the cell regardless of the concentration (FIG. 5).

In order to confirm the intact membrane integrity PI staining of the treated 3T3-L1 cells and the control was carried out. For this substance combinations with the following concentrations were used:

20 mg/ml, 30 mg/ml and 50 mg/ml phosphatidyl choline;
8 mg/ml, 12 mg/ml and 20 mg/ml glycyrrhizinate; and
72 mg/ml, 108 mg/ml and 180 mg/ml maltose.

The incubation period was 4 hours. Then the treated cells and two controls were incubated with 5 µg/ml PI for 5 minutes. The analysis was performed using the CLSM (FIG. 6).

The treatment of the cells with Triton X resulted in a damage of membrane integrity. That is why the propidium iodide was able to enter the cells and to stain the membrane destabilized cells. The positive control (FIG. 6b) showed, as expected, a staining of the cells permeabilized by Triton X. The untreated cells of the negative control (FIG. 6a) were not stained by PI. This indicates, that the membrane of these cells is intact.

The cells treated with 20 mg/ml PC (FIG. 6c) and 30 mg/ml PC (FIG. 6d) showed no staining by PI. Consequently, these cells showed no damage of the membrane and the used substance combinations no cytotoxic effect (FIG. 6 c, d).

The cells treated with 50 mg/ml PC (FIG. 6e) showed a weak red staining (FIG. 6e). These cells were treated with high doses of the substance combination. Thereby the medium was completely drawn from the cells and a lack of nutrients resulted, leading to cell damage at prolonged incubation. The weak staining of 50 mg/ml PC treated cells can therefore be attributed to the lack of nutrients and not to a damage of the cells due to phosphatidyl choline.

The substance combination of phosphatidyl choline, glycyrrhizinate and maltose showed in the performed in vitro experiments no membrane damaging effect. It should be noted, that for the detection of a potential membrane damage of the inventive substance combinations very high concentrations were used, which are significantly higher than the therapeutic used concentrations in vivo.

The relationship between an in vivo and in vitro effect is known as an in vivo/in vitro correlation. The determination of the in vivo/in vitro correlation is not trivial and behaves differently at various conditions. In many cases approximately an in vivo/in vitro correlation of ca. factor 100 can be assumed. This means, that concentrations used in vitro are about two decimal powers of ten less than the doses used in vivo to achieve similar effects. On this basis one would expect for example for Lipostabil® N for injection lipolysis the in vitro concentrations listed in Table 1.

TABLE 1

|  | In vivo used concentration in compound | Expected in-vitro concentration (factor 100) [mg/ml] | In vitro Cell damaging causing concentration |
| --- | --- | --- | --- |
| Na Deoxycholate | 12.65 mg/ml | 0.1265 | from 0.05 mg/ml |
| Phosphatidyl choline | 25 mg/ml | 0.25 | none |

TABLE 1-continued

|  | In vivo used concentration in compound | Expected in-vitro concentration (factor 100) [mg/ml] | In vitro Cell damaging causing concentration |
| --- | --- | --- | --- |
| Na-DC, PC from Lipostabil | 12.65 mg/ml Na-DC | 0.1265 | from 0.05 mg/ml Na-DC |
|  | 25 mg/ml PC | 0.25 | from 0.1 mg/ml PC |

In the case of Na-deoxycholate, both as a single agent as well as substance in Lipostabil®, the expected in vitro concentration according to the calculation agrees in terms of size with the concentrations determined in the experiments (Table 1). Therefrom it can be concluded that this substance has very likely a cell-damaging effect at the used concentration in the injection lipolysis.

Consequently, it is extremely unlikely that the concentrations of the substance combinations according to the invention used for an in vivo therapy will cause the same membrane damage of cells (and subsequent necrosis) as the ones from the state of the art. The same conversion factors can therefore be assumed for the combination of phosphatidyl choline and glycyrrhizic acid.

Example 7

In Vivo Studies on the Inflammatory Response of Treated Cells in the Mouse

Since inflammation is a trigger for the migration of adipose derived stem cells (ADSC), either a mixture (FIG. 8 d-f) containing phosphatidyl choline (PC), glycyrrhizic acid (GR) and maltose (MAL) (25 mg/ml PC, 10 mg/ml GR, 90 mg/ml of MAL), PBS buffer (FIG. 8 g-i) or E. coli cells (FIG. 8 a-c) was injected into the right subcutaneous adipose tissue of BALB/c mice. The incubation was 5 days.

Subsequently, it was stained for CD4, CD8, CD19 and CD20 to investigate the inflammatory response of the cells.

In addition, adipose derived stem cells (ADSC) were marked by a lentiviral expressing vector eGFP/luciferase and injected 48 hours after the initial injection into the opposite fatty tissue of the BALB/c mice.

The migration of ADSC cells was observed by bioluminescence. The results of Example 7 are shown in FIG. 8.

FIG. 8: Bioluminescence images of luciferase-labelled cells after subcutaneous injection of ADSC into the right fat tissue of Balb/c mice with:
(a-c) E. coli cells
(d-f) phosphatidyl choline+maltose+glycyrrhizinate (PMC)
(g-i) PBS-buffer After 48 hours luciferase-labelled ADSC cells were injected intraperitoneally in each case and the migration of ASC cells using bioluminescence was observed. In the mice (d-i) the ASC cells migrated into the liver and the spleen. In the mice (a-c) the ASC cells migrated to the region infected by the E. coli-injection and accumulated there.

In mice with PBS (FIG. 8 g-1) and in mice with the mixture containing PC (FIG. 8 d-f), no difference in the migration of ADSC cells was observed. In contrast, in mice which had been injected with E. coli, a migration and accumulation of ADSC cells in the region infected due to the E. coli injection was observed.

Consequently, here it was shown by luciferase-labelled adipose derived stem cells (ADSC) that an injection in vivo of a mixture containing phosphatidyl choline (PC), trisodium glycyrrhizinate and maltose causes no inflammatory reaction. This was demonstrated through the fact, that the luciferase-labelled ADSC cells did not migrate into or accumulate in the subcutaneous fat tissue, in which the mixture was injected.

These results confirm that phosphatidyl choline can be used as lipolytic active substance without triggering a severe inflammatory reaction when it is combined with glycyrrhizic acid.

Example 8

In Vitro Studies on the Lipolytic Action of the Substance Combination

3T3-L1 cells were stimulated by a hormone cocktail to adipogenesis and differentiated for another 8 days to mature adipocytes.

This was followed by a 4-hour incubation of cells with 10 mg/ml, 25 mg/ml and 50 mg/ml phosphatidyl choline and 4 mg/ml, 10 mg/ml and 20 mg/ml glycyrrhizinate and 36 mg/ml, 90 mg/ml and 180 mg/ml maltose The lipolytic activity was measured using a lipolysis assay, as described below:
Method of Lipolysis Assay:

The cleavage of triglycerides into glycerol and the three fatty acids is known as lipolysis. This process is catalyzed primarily by the hormone-sensitive lipase and the adipose triglyceride lipase. Using a lipolysis assay the lipolytic activity of cells can be detected. This assay is based on the measurement of glycerol emerged during lipolysis, which is secreted by the cells into the medium. The glycerol is metabolized by enzymatic reactions to glycerol-1-phosphate and then to dihydroxy acetone phosphate. Thereby hydrogen peroxide is produced, which is quantified photometrically with a peroxidase stain reaction. In order to be able to make statements about the lipolytic action of substances, they are compared with the basal lipolysis activity of the cells and with the lipolysis stimulated by the beta-adrenergic receptor. Such a stimulation can be caused by isoproterenol.

Figure 7:
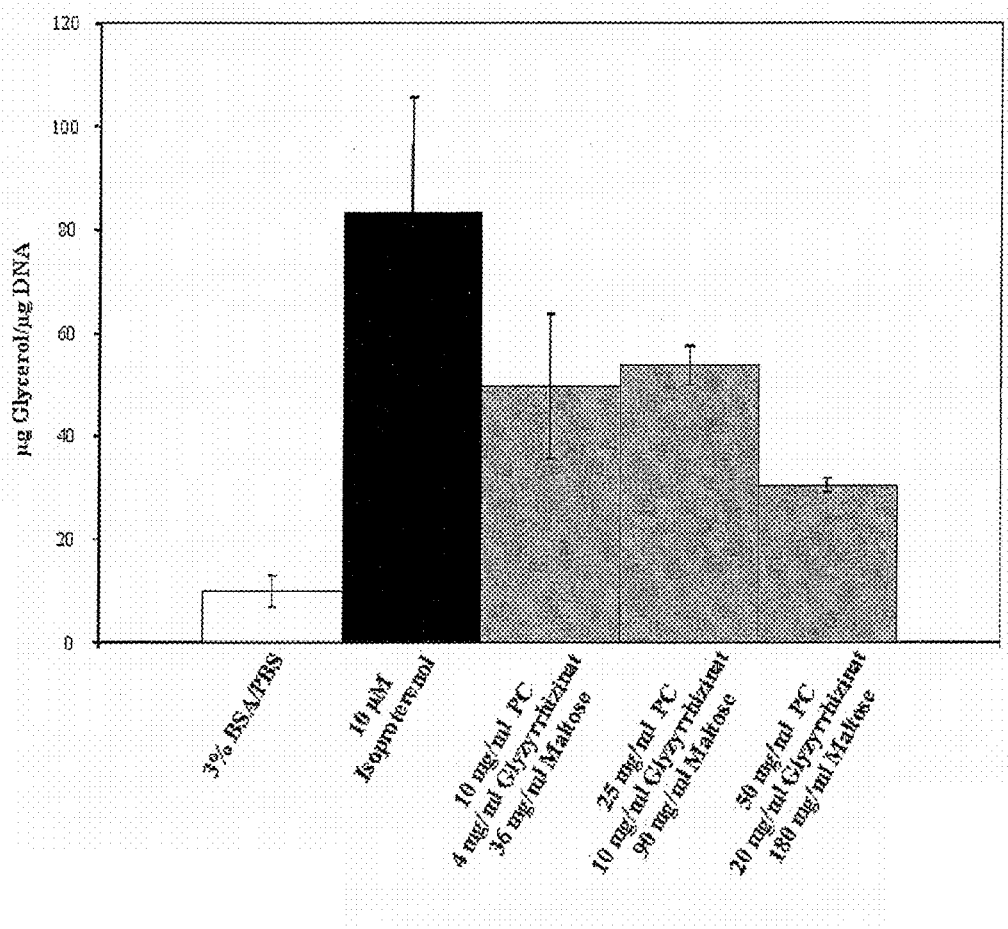
FIG. 7 is a graphical representation the analysis of the lipolysis assay with treated differentiated 3T3-L1 cells.

The results of Example 8 are shown in FIG. 7.

FIG. 7: Graphical picture of the analysis of the lipolysis assay (µg glycerol/µg DNA) with treated differentiated 3T3-L1 cells. 3T3-L1 were stimulated by a hormonal induction cocktail to adipogenesis and then differentiated for 8 days. The treatment of the mature adipocytes was carried out for 4 hours respectively in 3% BSA/PBS with:

10 µM isoproterenol (positive control for stimulated lipolysis)

10 mg/ml phosphatidyl choline+4 mg/ml glycyrrhizinate+36 mg/ml maltose 25 mg/ml phosphatidyl choline+10 mg/ml glycyrrhizinate+90 mg/ml maltose 50 mg/ml phosphatidyl choline+20 mg/ml glycyrrhizinate+180 mg/ml maltose As a control for the basal lipolysis activity untreated cells in 3% BSA/PBS were used. The bars indicate the standard deviation of n=3. The experiment was conducted twice. (PC=phosphatidyl choline)

The first bar in FIG. 7 shows, that the basal lipolysis activity of untreated cells in 3% BSA/PBS is at 8 µg glycerol/µg of DNA. Based on this basal level the lipolysis activity of the other samples was determined. In the positive control (FIG. 7) a stimulation of lipolysis was induced by 10 µM of the β-adrenoceptor agonist isoproterenol. The positive control shows a lipolytic activity, which increases to eight times the basal level. All cells treated with the substance combination (10 mg/ml, 25 mg/ml and 50 mg/ml PC) showed an increased lipolytic activity compared to the basal level (FIG. 7). A treatment of cells with the substance combination containing 10 or 25 mg/ml PC resulted in an 5-times increased lipolysis activity compared to the basal level. The treatment of the cells with the substance combination containing 50 mg/ml of PC led to a 3-times increased lipolysis activity in comparison to the basal level (FIG. 7). The decrease in the lipolytic activity at the highest concentration is probably, as already explained, due to the fact that the cells have a lack of nutrients because of the withdrawal of medium, which is necessary to them to survive or to maintain the normal functions, such as the lipolytic activity.

The inventive substance combination shows in vitro a marked lipolytic effect.

Comparative Example 1

Lipostabil® Containing Phosphatidyl Choline and Sodium Deoxycholate

Na-deoxycholate concentrations of 0.005-0.5 mg/ml (effect as a single substance from 0.05 mg/ml) and phosphatidyl choline concentrations of 0.01-1 mg/ml (no effect as a single substance) were used.

The procedure was analogous to Example 8

Figure 9:
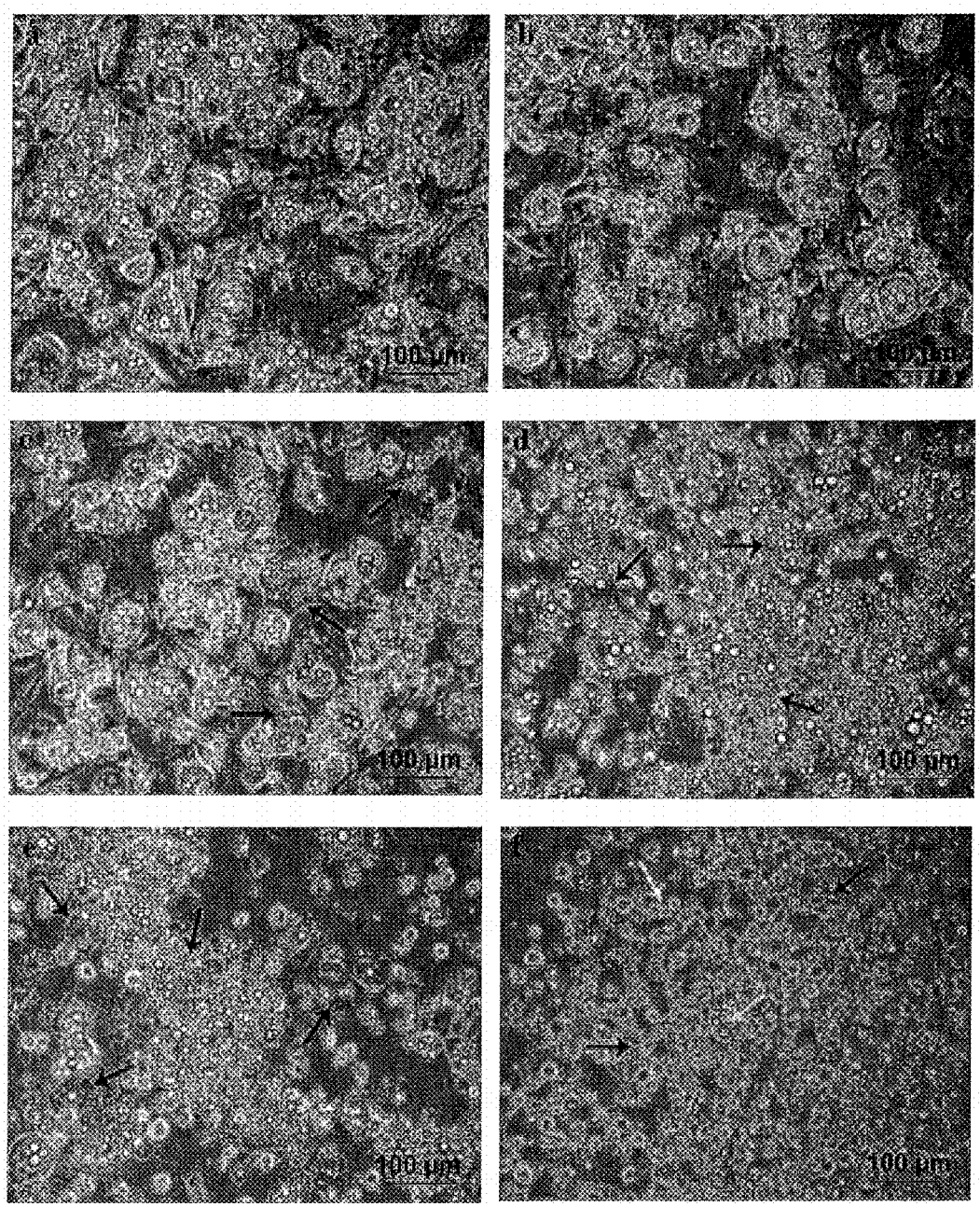
FIG. 9 depicts phase contrast images of treated differentiated 3T3-L1 cells.

The results of Comparative Example 1 are shown in FIG. 9.

FIG. 9: Phase contrast images of treated differentiated 3T3-L1 cells. 3T3-L1 were stimulated by a hormonal induction cocktail to adipogenesis and then differentiated for 8 days. The mature adipocytes were treated for 24 hours with phosphatidyl choline and sodium deoxycholate from Lipostabil® with the following concentrations:

(a) untreated cells in differentiation medium,
(b) 0.01 mg/ml phosphatidyl choline+0.005 mg/ml Na-deoxycholate,
(c) 0.1 mg/ml phosphatidyl choline+0.05 mg/ml Na-deoxycholate,
(d) 0.25 mg/ml phosphatidyl choline+0.125 mg/ml Na-deoxycholate,
(e) 0.5 mg/ml phosphatidyl choline+0.25 mg/ml Na-deoxycholate,
(f) 1 mg/ml phosphatidyl choline+0.5 mg/ml Na-deoxycholate.

The analysis was done using the light microscope. Cells with damaged membrane or cell fragments are marked examplary with black arrows, while free lipid droplets are indicated by white arrows.

While the lowest concentration of phosphatidyl choline and sodium deoxycholate still showed no effect (FIG. 9b), at the next higher one a slight injury of the cells was visible (FIG. 5c), which was enhanced with increasing concentration. In FIG. 5e the cell membranes are strongly affected, indicating that Lipostabil® at a concentration of 0.5 mg/ml phosphatidyl choline together with 0.25 mg/ml sodium deoxycholate strongly damaged the cells and caused cell death by necrosis. The nature of the effect of Lipostabil® was more comparable to the detergent action of the Na-deoxycholate (typical damage to cell membrane), which effect is obviously more important. Such a typical membrane damaging effect of phosphatidyl choline as a single agent could not be detected, suggesting that the cytotoxic effect in Lipostabil® primarily emanates from Na-deoxycholate. The comparison of the effective concentration ranges of Lipostabil® with those of the individual substances supports the conclusion with regard to the preponderance effect of Na-deoxycholate. Whereas the phosphatidyl choline as a single agent was not effective, the Lipostabil® achieved already at a concentration of 0.1 mg/ml of phosphatidyl choline slight effects (at this concentration no effects of the PC as a single agent). However, Na-deoxycholate as a single dose at a concentration from 0.05 mg/ml caused already initial membrane damages, which also occurred with Lipostabil® at this concentration.

Example 9

Administration of Phosphogliv® and Lipostabil® to Female Test Persons, snd Determination of the Efficacy of Subcutaneous Lipolysis The preparation Phosphogliv® i.v. used so far for liver disease contains instead of DC (as in Lipostabil® N i.v.)

glycyrrhizic acid. First experimental results and studies on two test persons indicated an equal efficacy of the preparation as with Lipostabil® N i.v. at significantly better tolerance.

The experiments described herein demonstrate a comparable effect of Phosphogliv® to Lipostabil® with a better tolerance of Phosphogliv®.

In a prospective, controlled study, six female test persons were treated at the left upper arm with Phosphogliv® and at the right upper arm with Lipostabil®.

The used ampoules contained 0.5 g PPC, 0.2 g glycyrrhizinate and 1.8 g maltose as a lyophilisate, to be dissolved in 10 ml of water per injection. Depending on the extent of the area to be injected up to 60 subcutanous punctures were made on each upper arm, 0.5 ml at a distance of 1.5 cm respectively.
Investigation Times of Effects of the Preparations:

The treatment lasted 16 weeks. The investigations were performed one day before the start of treatment (t=−1), on the day of first treatment (t=0), eight weeks after starting treatment (t=8) and 16 weeks after starting treatment (t=16).
Determination an Effect To detect an effect the circumference of the upper arm of the test persons was measured. The circumference of upper arm [cm] was measured using a caliper (Caliper) and measuring tape (myo-tape) before treatment and after eight and 16 weeks.

In addition, the blood fats total cholesterol, LDL-cholesterol and HDL-cholesterol in mg/dl and the atherogenic index of LDL- to HDL-cholesterol were determined.
Presentation of Results From the measured values, the measured value changes as difference from baseline and the change in percent from baseline average values and standard deviation were determined.

The circumference of the upper arms of the test persons differed depending on the chosen method of measurement caliper or myo-type caliper. Regardless of the method used, in each case a decrease of the upper arm circumference was detectable. Between the effects of Phosphogliv® and Lipostabil® there was no difference evident. Both compounds induced a reduction of the upper arm circumference to the same extent (see Table 3-1 and 3-2).

TABLE 3-1 circumference of the upper arm measured with Caliper [cm]

| | | Time in weeks after start of the treatment with | | | | | | |
|---|---|---|---|---|---|---|---|---|
| | | Phosphogliv ® (left) | | | | Lipostabil ® (right) | | |
| test person | | −1 | 0 | 8 | 16 | −1 | 0 | 8 | 16 |
| 6 | I.B. | 3.1 | 3.1 | 2.6 | 2.5 | 3.1 | 3.1 | 2.7 | 2.5 |
| 2 | Ch.K. | 2.9 | 2.9 | 2.2 | 2.0 | 2.9 | 2.9 | 2.2 | 2.0 |
| 7 | S.A. | 3.2 | 3.2 | 2.8 | 2.7 | 3.3 | 3.3 | 2.9 | 2.8 |
| 1 | G.E. | 3.8 | 3.8 | 3.2 | 2.8 | 3.8 | 3.8 | 3.2 | 2.8 |
| 3 | M.St. | 2.9 | 2.9 | 2.6 | 2.5 | 3.0 | 3.0 | 2.7 | 2.6 |
| 4 | E.K. | 2.2 | 2.2 | 1.4 | | 2.3 | 2.3 | 1.5 | |
| | average | 3.02 | 3.02 | 2.47 | 2.50 | 3.07 | 3.07 | 2.53 | 2.54 |
| | standard deviation | 0.52 | 0.52 | 0.62 | 0.31 | 0.49 | 0.49 | 0.60 | 0.33 |
| | N | 6 | 6 | 6 | 5 | 6 | 6 | 6 | 5 |

TABLE 2 raw data

| | | | | | | | Compound | | | | |
|---|---|---|---|---|---|---|---|---|---|---|---|
| test person | | Time [t] | P Cal li [cm] | L Cal re [cm] | P Myo li [cm] | L Myo re [cm] | total cholesterol [md/dl] | LDL-cholesterol [mg/dl] | HDL-cholesterol [mg/dl] | clinical improvement | remarks |
| No. | | | | | | | | | | | |
| 6 | I.B. | −1 | 3.1 | 3.1 | 35.0 | 35.0 | 269.0 | 169.0 | 53.8 | | |
| | I.B. | 0 | 3.1 | 3.1 | 35.0 | 35.0 | | | | | |
| | I.B. | 8 | 2.6 | 2.7 | 32.5 | 33.0 | 159.0 | 112.0 | 58.9 | DeI/DeIP | Ezetrol-taking probable |
| | I.B. | 16 | 2.5 | 2.5 | 32.0 | 32.0 | 172.0 | 127.0 | 58.3 | DeI/DeIP | |
| 2 | Ch.K. | −1 | 2.9 | 2.9 | 30.5 | 30.5 | 237.0 | 136.0 | 75.4 | | |
| | Ch.K. | 0 | 2.9 | 2.9 | 30.5 | 30.5 | | | | | |
| | Ch.K. | 8 | 2.2 | 2.2 | 28.2 | 29.0 | 222.0 | 129.0 | 78.0 | DrI/DrIP | |
| | Ch.K. | 16 | 2.0 | 2.0 | 28.0 | 28.5 | 218.0 | 128.0 | 79.0 | DrI/DrIP | |
| 7 | S.A. | −1 | 3.2 | 3.3 | 31.0 | 32.0 | 212.0 | 104.0 | 88.4 | | |
| | S.A. | 0 | 3.2 | 3.3 | 31.0 | 32.0 | | | | | |
| | S.A. | 8 | 2.8 | 2.9 | 27.0 | 28.5 | 214.0 | 103.0 | 89.1 | DrI/DrIP | |
| | S.A. | 16 | 2.7 | 2.8 | 26.0 | 27.0 | | | | DrI/DrIP | |
| 1 | G.E. | −1 | 3.8 | 3.8 | 33.0 | 33.0 | 143.0 | 53.0 | 67.0 | | |
| | G.E. | 0 | 3.8 | 3.8 | 33.0 | 33.0 | | | | | |
| | G.E. | 8 | 3.2 | 3.2 | 31.8 | 31.8 | 141.0 | 51.0 | 68.0 | DeI/DeIP | |
| | G.E. | 16 | 2.8 | 2.8 | 30.5 | 30.5 | 142.0 | 49.0 | 54.0 | DeI/DeIP | |
| 3 | M.St. | −1 | 2.9 | 3.0 | 35.0 | 36.0 | 198.0 | 120.2 | 62.8 | | |
| | M.St. | 0 | 2.9 | 3.0 | 35.0 | 36.0 | | | | | |
| | M.St. | 8 | 2.6 | 2.7 | 33.0 | 32.5 | 182.0 | 110.0 | 60.3 | DeI/DeIP | |
| | M.St. | 16 | 2.5 | 2.6 | 32.0 | 32.0 | 182.0 | 110.9 | 60.8 | DeI/DeIP | |
| 4 | E.K. | −1 | 2.2 | 2.3 | 28.5 | 29.0 | 187.0 | 99.0 | 68.7 | | |
| | E.K. | 0 | 2.2 | 2.3 | 28.5 | 29.0 | | | | | |
| | E.K. | 8 | 1.4 | 1.5 | 26.0 | 27.0 | 177.0 | 92.0 | 69.3 | DrI/DrIP | |
| | E.K. | 16 | | | | | | | | | |

Cal li = Caliper left; Cal re = Caliper right; Myo li = Myo-type left; Myo re = Myo-type right; P = Phosphogliv ®; L = Lipostabil ®: DeI = Definite improvement of efficacy and compatibility. physician; DeIP = Definite improvement of efficacy and compatibility. patient; DrI = Dramatic improvement of efficacy and compatibility. physician; DrIP = Dramatic improvement of efficacy and compatibility. patient

TABLE 3-2

Change in the circumference of the upper arm measured with caliper in cm as absolute and relative difference compared to week 0

| | | Time in weeks after start of the treatment with | | | | | | | |
|---|---|---|---|---|---|---|---|---|---|
| | | Phosphogliv ® (left) | | | | Lipostabil ® (right) | | | |
| | | 8 | | 16 | | 8 | | 16 | |
| test person | | cm | % | cm | % | cm | % | cm | % |
| 6 | I.B. | −0.5 | −16.1 | −0.6 | −19.4 | −0.4 | −12.9 | −0.6 | −19.4 |
| 2 | Ch.K. | −0.7 | −24.1 | −0.9 | −31.0 | −0.7 | −24.1 | −0.9 | −31.0 |
| 7 | S.A. | −0.4 | −12.5 | −0.5 | −15.6 | −0.4 | −12.1 | −0.5 | −15.2 |
| 1 | G.E. | −0.6 | −15.8 | −1.0 | −26.3 | −0.6 | −15.8 | −1.0 | −26.3 |
| 3 | M.St. | −0.3 | −10.3 | −0.4 | −13.8 | −0.3 | −10.0 | −0.4 | −13.3 |
| 4 | E.K. | −0.8 | −36.4 | | | −0.8 | −34.8 | | |
| | average | −0.55 | −19.21 | −0.68 | −21.22 | −0.53 | −18.29 | −0.68 | −21.04 |
| | standard deviation | 0.19 | 9.63 | 0.26 | 7.28 | 0.20 | 9.47 | 0.26 | 7.49 |
| | N | 6 | 6 | 5 | 5 | 6 | 6 | 5 | 5 |

It is clear from table 3-2 that by using caliper due to Lipostabil® and Phosphogliv® after 8 weeks a reduction of the upper arm circumference of 19.21% and 18.29% took place. After 16 weeks, a reduction of the upper arm circumference of 21.22% and 21.04% was determined using caliper. Consequently, both compounds Phosphogliv® and Lipostabil® have the same efficacy.

TABLE 4-1

Circumference of the upper arm measured with Myo-tape [cm]

| | | Time in weeks after start of the treatment with | | | | | | | |
|---|---|---|---|---|---|---|---|---|---|
| | | Phosphogliv ® (left) | | | | Lipostabil ® (right) | | | |
| test person | | −1 | 0 | 8 | 16 | −1 | 0 | 8 | 16 |
| 6 | I.B. | 35.0 | 35.0 | 32.5 | 32.0 | 35.0 | 35.0 | 33.0 | 32.0 |
| 2 | Ch.K. | 30.5 | 30.5 | 28.2 | 28.0 | 30.5 | 30.5 | 29.0 | 28.5 |
| 7 | S.A. | 31.0 | 31.0 | 27.0 | 26.0 | 32.0 | 32.0 | 28.5 | 27.0 |
| 1 | G.E. | 33.0 | 33.0 | 31.8 | 30.5 | 33.0 | 33.0 | 31.8 | 30.5 |
| 3 | M.St. | 35.0 | 35.0 | 33.0 | 32.0 | 36.0 | 36.0 | 32.5 | 32.0 |
| 4 | E.K. | 28.5 | 28.5 | 26.0 | | 29.0 | 29.0 | 27.0 | |
| | average | 32.17 | 32.17 | 29.75 | 29.70 | 32.58 | 32.58 | 30.30 | 30.00 |
| | standard deviation | 2.62 | 2.62 | 3.04 | 2.64 | 2.65 | 2.65 | 2.46 | 2.21 |
| | N | 6 | 6 | 6 | 5 | 6 | 6 | 6 | 5 |

TABLE 4-2

Change in the circumference of the upper arm measured with Myo-type in cm as absolute and relative difference compared to week 0

| | | Time in weeks after start of the treatment with | | | | | | | |
|---|---|---|---|---|---|---|---|---|---|
| | | Phosphogliv ® (left) | | | | Lipostabil ® (right) | | | |
| | | 8 | | 16 | | 8 | | 16 | |
| test person | | cm | % | cm | % | cm | % | cm | % |
| 6 | I.B. | −2.5 | −7.1 | −3.0 | −8.6 | −2.0 | −5.7 | −3.0 | −8.6 |
| 2 | Ch.K. | −2.3 | −7.5 | −2.5 | −8.2 | −1.5 | −4.9 | −2.0 | −6.6 |
| 7 | S.A. | −4.0 | −12.9 | −5.0 | −16.1 | −3.5 | −10.9 | −5.0 | −15.6 |
| 1 | G.E. | −1.2 | −3.6 | −2.5 | −7.6 | −1.2 | −3.6 | −2.5 | −7.6 |
| 3 | M.St. | −2.0 | −5.7 | −3.0 | −8.6 | −3.5 | −9.7 | −4.0 | −11.1 |
| 4 | E.K. | −2.5 | −8.8 | | | 2.0 | −6.9 | | |
| | average | −2.42 | −7.62 | −3.20 | −9.81 | −2.28 | −6.97 | −3.30 | −9.89 |
| | standard deviation | 0.92 | 3.13 | 1.04 | 3.56 | 0.99 | 2.84 | 1.20 | 3.63 |
| | N | 6 | 6 | 5 | 5 | 6 | 6 | 5 | 5 |

It is clear from table 4-2 that due to Lipostabil® and Phosphogliv® after 8 weeks. a reduction of the upper arm circumference of 7.62% and 6.97% according to the myo-tape method occurred. After 16 weeks a reduction of the upper arm circumference of 9.81% and 9.89% by myo-tape was determined. Consequently. both preparations Phosphogliv® and Lipostabil® have the same efficiency.

Although both methods caliper and myo-tape show different reductions by the compounds. the degree of effectiveness of both preparations Lipostabil® and Phosphogliv® is equivalent.

Example 10

Assessment of Side Effects from Treatment with Lipostabil® and Phosphogliv®

For this purpose, the female test persons were treated as described in Example 9 and the effectiveness was examined. In order to document the side effects. images of the upper arms of the female test persons before and after treatment with Phosphogliv® and Lipostabil® were made (FIGS. 10 and 11).

After 3 minutes a marked redness and swelling on the right upper arm of test person No. 1. which was treated with Lipostabil® was determined. In comparison thereto. at the left upper arm which was treated with Phosphogliv® only a slight redness and swelling was determined. This phenotype confirms the results of the in vitro experiments to phosphatidyl choline. which has no membrane damaging effect on the cells (Example 5. FIG. 4*a-c*)). The images of test person No. 02 in FIG. 11 show the same difference between the left (Phosphogliv®) and right (Lipostabil®) upper arm.

FIG. 10: Photographic documentation after treatment of the left (Phosphogliv®) and right (Lipostabil®) upper arm of the test person No. 01. The imges weer made 3 minutes after administration of the preparations Lipostabil® and Phosphogliv®.

FIG. 11: Photographic documentation after treatment of the left (Phosphogliv®) and right (Lipostabil®) upper arm of the test person No. 02. The images were made 3 minutes after the administration of the preparations Lipostabil® and Phosphogliv®.

Furthermore. the side effects were summarized in table 5 below.

TABLE 5

| | Side effects due to treatment with Phosphogliv ® and Lipostabil ® | | | | | |
|---|---|---|---|---|---|---|
| | t = 0 | | t = 8 | | t = 16 | |
| test pers. | P | L | P | L | P | L |
| No. 1 | | | Only short pain. nearly no swelling | Substantial swelling and pain. up to 3 days | Hardly any pain | Swelling. reddening until 4$^{th}$ day |
| No. 2 | | | Much less swelling and reddening | Much more reddening and swelling | Hardly any pain | Pain for 1 week |
| No. 3 | Just nothing | Burning and itching for 5 min. light pain over 2 weeks | „a piece of cake" = no pain at all | Light pain over the first 2 weeks | No unexpeteced reaction. much less complaints | No unexpected reaction. much more complaints |
| No. 4 | | | Only for about 3 minutes pain in the injected area. swelling and reddening for 3 days. Thereafter. no pain or swelling | Much more pain. swelling during the first 3 days about the same as with Phosphogliv. Duration of swelling and reddening for 12 days. Sensibility with Lipostabil lasted nearly all 8 weeks | | |
| No. 6 | | | Hardly any pain | | No complaints | Swelling and reddening up to 3 days |
| No. 7 | | | Hardly any pain | | Pain and swelling on both arms easily bearable | |

P = Phosphogliv ®; L = Lipostabil ®

Doctor and test person mentioned after the first and second treatment in all cases uniformly a clear or dramatic improvement (reduction) of the upper arm fat pads with both preparations as also a significantly better tolerance to Phosphogliv. The skin resistance was good in all cases after treatment.

The data in table 5 show that complaints of the test persons after treatment with Lipostabil® involve swelling. redness and pain at the injection sites. Such side effects occur little or not at all during treatment with Phosphogliv® Thus, Phosphogliv® was significantly better tolerated by the questioned test persons than the preparation Lipostabil®. As mentioned before. the better tolerance is attributed to the reduced or not occurring cell damage. As shown in Example 5, phosphatidyl choline does not damage the cell membrane while the sodium deoxycholate from Lipostabil® damages the cells.

Example 11

Determination of Cholesterol Levels Before and after Subcutaneous Lipolysis

For this the blood fats of the test persons were observed over the therapy period. The total cholesterol. LDL (low-density lipoprotein) cholesterol and HDL-(high-density lipoprotein) cholesterol were determined. Table 6 summarizes the values at the time of t=−1. t=8 weeks and t=16 weeks.

On average the blood fats changed over the therapy period in the same direction. Only in case of the two test persons (IB and Ch.K.) with significantly increased total cholesterol and LDL-cholesterol the values descended. while the HDL-cholesterol (Table 6) ascended. A summary of the study is shown in table 7.

The other biochemical control variables AST. ALT. γ-GT. bilirubine. creatinine and glucose remained within the normal range. except a slight increase in γ-GT value in test person S.A. before starting treatment. within the normal range.

TABLE 6

Cholesterol values [mg/dl]

| Test person | | total cholesterol | | | LDL-cholesterol | | | HDL-cholesterol | | |
|---|---|---|---|---|---|---|---|---|---|---|
| | | −1 | 8 | 16 | −1 | 8 | 16 | −1 | 8 | 16 |
| 6 | I.B. | 269.0 | 159.0 | 172.0 | 169.0 | 112.0 | 127.0 | 53.8 | 58.9 | 58.3 |
| 2 | Ch.K. | 237.0 | 222.0 | 218.0 | 136.0 | 129.0 | 128.0 | 75.4 | 78.0 | 79.0 |
| 7 | S.A. | 212.0 | 214.0 | | 104.0 | 103.0 | | 88.4 | 89.1 | |
| 1 | G.E. | 143.0 | 141.0 | 142.0 | 53.0 | 51.0 | 49.0 | 67.0 | 68.0 | 54.0 |
| 3 | M.St. | 198.0 | 182.0 | 182.0 | 120.2 | 110.0 | 110.9 | 62.8 | 60.3 | 60.8 |
| 4 | E.K. | 187.0 | 177.0 | | 99.0 | 92.0 | | 68.7 | 69.3 | |
| Average | | 207.67 | 182.50 | 178.50 | 113.53 | 99.50 | 103.73 | 69.35 | 70.60 | 63.03 |
| Standard deviation | | 43.23 | 31.17 | 31.34 | 38.97 | 26.67 | 37.32 | 11.75 | 11.39 | 11.01 |
| N | | 6 | 6 | 4 | 6 | 6 | 4 | 6 | 6 | 4 |

LDL/HDL-Quotient  −1 week  1.64
(target value < 3)  8 weeks  1.41
                   16 weeks  1.65
LDL-Cholesterol = Low-Density-Lipoproteine-cholesterol
HDL-cholesterol = High-Density-Lipoprotein-cholesterol

TABLE 7

Summary of the results of the study with the test persons

| Test person | | Time | Caliper [cm] | | Myo-type | | clinical improvements | remarks |
|---|---|---|---|---|---|---|---|---|
| | | | left Phosphogliv | right Lipostabil | left Phosphogliv | right Lipostabil | | |
| 6 | I.B. | Screening | 3.1 | 3.1 | 35 | 35 | | * Ezetrol taking probable |
| | | 0 | 3.1 | 3.1 | 35 | 35 | | |
| | | 8 | 2.6 | 2.7 | 32.5 | 33 | DeI/DeIP | total cholesterol from 269.0 mg/dl to 159.0 mg/dl |
| | | | | | | | | LDL-cholesterol from 169.0 mg/dl to 112.0 mg/dl |
| | | | | | | | | HDL-cholesterol from 53.8 mg/dl to 58.9 mg/dl |
| | | 16 | 2.5 | 2.5 | 32 | 32 | DeI/DeIP | total cholesterol from 159.0 mg/dl to 172.0 mg/dl |
| | | | | | | | | LDL-cholesterol from 112.0 mg/dl to 127.0 mg/dl |
| | | | | | | | | HDL-cholesterol from 58.9 mg/dl to 58.3 |
| | | | | | | | | Left no complaints. right up to 3 days pain |
| | | | | | | | | Skin tightness improved from moderate to good |
| 2 | Ch.K. | Screening | 2.9 | 2.9 | 30.5 | 30.5 | | |
| | | 0 | 2.9 | 2.9 | 30.5 | 30.5 | | |
| | | 8 | 2.2 | 2.2 | 28.2 | 29 | DrI/DrIP | total cholesterol from 237.0 mg/dl to 222.0 mg/dl |
| | | | | | | | | LDL-cholesterol from 136.0 mg/dl to 129.0 mg/dl |
| | | | | | | | | HDL-cholesterol from 75.4 mg/dl to 78.0 m./dl |
| | | 16 | 2.0 | 2.0 | 28 | 28.5 | DrI/DrIP | total cholesterol from 222 mg/dl to 218 mg/dl |
| | | | | | | | | LDL-cholesterol from 129.0 mg/dl to 128.0 mg/dl |
| | | | | | | | | HDL-cholesterol from 78.0 mg/dl to 79.0 mg/dl |
| | | | | | | | | Left nearly no pain. right for about 1 week |
| | | | | | | | | Skin tightness good from the beginning |

TABLE 7-continued

Summary of the results of the study with the test persons

| Test person | | Time | Caliper [cm] | | Myo-type | | clinical improvements | remarks |
|---|---|---|---|---|---|---|---|---|
| | | | left Phosphogliv | right Lipostabil | left Phosphogliv | right Lipostabil | | |
| 3 | M. St. | Screening | 2.9 | 3.0 | 35 | 36 | | |
| | | 0 | 2.9 | 3.0 | 35 | 36 | | |
| | | 8 | 2.6 | 2.7 | 33 | 32.5 | DeI/DeIP | total cholesterol from 198.0 mg/dl to 182.0 mg/dl<br>LDL-cholesterol from 120.2 mg/dl to 110.0 mg/dl<br>HDL-cholesterol from 62.8 mg/dl to 60.3 mg/dl |
| | | 16 | 2.5 | 2.6 | 32 | 32 | DeI/DeIP | total cholesterol from 182.0 mg/dl auf 182.0 mg/dl<br>LDL-cholesterol from 110.0 mg/dl to 110.9 mg/dl<br>HDL-cholesterol from 60.3 mg/dl to 60.8 mg/dl<br>Skin tightness improved from moderate to good |
| 4 | E.K. | Screening | 2.2 | 2.3 | 28.5 | 29 | | |
| | | 0 | 2.2 | 2.3 | 28.5 | 29 | | |
| | | 8 | 1.4 | 1.5 | 26 | 27 | DrI/DrIP | total cholesterol from 187.0 mg/dl to 177.0 mg/dl<br>LDL-cholesterol from 99.0 mg/dl to 92.0 mg/dl<br>HDL-cholesterol from 68.7 mg/dl to 69.3 mg/dl<br>Skin tightness good from the beginning |
| 7 | S.A. | Screening | 3.2 | 3.3 | 31 | 32 | | |
| | | 0 | 3.2 | 3.3 | 31 | 32 | | |
| | | 8 | 2.8 | 2.9 | 27 | 28.5 | DrI/DrIP | total cholesterol from 212.0 mg/dl to 214.0 mg/dl<br>LDL-cholesterol from 104.0 mg/dl to 103.0 mg/dl<br>HDL-cholesterol from 88.4 mg/dl to 89.1 mg/dl |
| | | 16 | 2.7 | 2.8 | 26 | 27 | DrI/DrIP | γ-GT normalized<br>Skin tightness good from the beginning |
| 1 | G.E. | Screening | 3.8 | 3.8 | 33 | 33 | | |
| | | 0 | 3.8 | 3.8 | 33 | 33 | | |
| | | 8 | 3.2 | 3.2 | 31.8 | 31.8 | DeI/DeIP | total cholesterol from 143.0 mg/dl to 141.0 mg/dl<br>LDL-cholesterol from 53.0 mg/dl to 51.0 mg/dl<br>HDL-cholesterol from 67.0 mg/dl to 68.0 mg/dl |
| | | 16 | 2.8 | 2.8 | 30.5 | 30.5 | DeI/DeIP | total cholesterol from 141.0 mg/dl to 142.0 mg/dl<br>LDL-cholesterol from 51.0 mg/dl to 49.0 mg/dl<br>HDL-cholesterol from 68.0 mg/dl to 54.0 mg/dl<br>Skin tightness good from the beginning |

DeI = Definite improvement of efficacy and compatibility. physician;
DeIP = Definite improvement of efficacy and compatibility. patient;
DrI = Dramatic improvement of efficacy and compatibility. physician;
DrIP = Dramatic improvement of efficacy and compatibility. patient

The invention claimed is:

1. A method for the non-surgical removal of a subcutaneous fat accumulation, from the adipose tissue of a patient in need thereof, the method comprising:
providing a composition comprising one or more phospholipids derived from soybeans and one or more of glycyrrhizic acid and its physiologically acceptable salts, wherein the total content of the one or more phospholipids derived from soybeans and the one or more of glycyrrhizic acid and its physiologically acceptable salts in the composition is 2-80 weight percent, and wherein the weight ratio between the one or more phospholipids derived from soybeans and the one or more of glycyrrhizic acid and its physiologically acceptable salts is from 4:1 to 1:1; the composition being in the form of a liposome-micelle water-system with a particle size in the range of from 30 nm to 180 nm; and administering an amount of the composition to the patient, by subcutaneous, intraperitoneal, intramuscular or intravenous injection, the amount sufficient to non-surgically remove the subcutaneous fat accumulation, from the adipose tissue of the patient in need thereof.

2. The method according to claim 1 wherein the one or more phospholipids includes phosphatidyl choline.

3. The method according to claim 1 wherein the composition includes one or more selected from the group consisting of glycyrrhizic acid, a potassium salt of glycyrrhizic acid, a sodium salt of glycyrrhizic acid, an ammonium salt of glycyrrhizic acid and a magnesium salt of glycyrrhizic acid.

4. The method according to claim 1 wherein the composition further comprises a sugar selected from the group consisting of glucose, maltose, mannitol, sorbitol, lactose and derivatives thereof.

5. The method according to claim 1 wherein 15 to 98 weight percent of the one or more phospholipids in the composition is phosphatidyl choline.

6. The method according to claim 1 wherein the composition is prepared for administration by dissolving a dry form of the one or more phospholipids and the one or more of glycyrrhizic acid and its salts in a suitable solvent.

7. The method according to claim 6 wherein the dry form of the one or more phospholipids and the one or more of glycyrrhizic acid and its salts is obtained as a lyophilisate by freeze-drying.

8. The method according to claim 1 wherein the composition is administered in the form of a solution.

9. The method according to claim 1 wherein the composition further comprises one or more physiologically suitable solvents.

10. The method according to claim 1 wherein the subcutaneous fat accumulations removed are one more selected from the group consisting of lipedemas, lipomas, lipomatosis of the abdomen, dermatopanniculosis deformans, pseudogynecomastia, a Buffalo Hump in HIV patients, cellulitis, and nonspecific subcutaneous fat deposits.

* * * * *